(12) United States Patent
Schinagl et al.

(10) Patent No.: US 10,613,100 B2
(45) Date of Patent: Apr. 7, 2020

(54) ANTI-MIF IMMUNOHISTOCHEMISTRY

(71) Applicants: Baxalta Incorporated, Bannockburn, IL (US); Baxalta GmbH, Glattpark (Opfikon) (CH)

(72) Inventors: Alexander Schinagl, Vienna (AT); Michael Thiele, Vienna (AT); Patrice Douillard, Vienna (AT); Gerhard Antoine, Gross Enzersdorf (AT); Randolf Kerschbaumer, Klosterneuburg (AT)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 277 days.

(21) Appl. No.: 15/109,411

(22) PCT Filed: Jan. 2, 2015

(86) PCT No.: PCT/EP2015/050005
§ 371 (c)(1),
(2) Date: Jun. 30, 2016

(87) PCT Pub. No.: WO2015/106973
PCT Pub. Date: Jul. 23, 2015

(65) Prior Publication Data
US 2016/0334414 A1    Nov. 17, 2016

Related U.S. Application Data

(60) Provisional application No. 61/923,464, filed on Jan. 3, 2014.

(51) Int. Cl.
| | | |
|---|---|---|
| G01N 33/68 | (2006.01) | |
| C07K 16/42 | (2006.01) | |
| C07K 16/24 | (2006.01) | |
| G01N 33/53 | (2006.01) | |
| A61K 39/00 | (2006.01) | |

(52) U.S. Cl.
CPC ......... G01N 33/6863 (2013.01); C07K 16/24 (2013.01); C07K 16/4208 (2013.01); C07K 16/4241 (2013.01); A61K 2039/505 (2013.01); C07K 2317/55 (2013.01); G01N 2333/52 (2013.01)

(58) Field of Classification Search
None
See application file for complete search history.

(56) References Cited

U.S. PATENT DOCUMENTS

| | | |
|---|---|---|
| 6,645,493 B1 | 11/2003 | Bucala et al. |
| 2003/0235584 A1 | 12/2003 | Kloetzer et al. |

FOREIGN PATENT DOCUMENTS

| | | |
|---|---|---|
| WO | WO 200908692 | 7/2009 |
| WO | WO 2013050453 | 4/2013 |
| WO | WO 2013156472 | 10/2013 |
| WO | WO 2014009355 | 1/2014 |

OTHER PUBLICATIONS

Paul, Fundamental Immunology, (textbook), 1993, pp. 292-295 (Year: 1993).*
Rudikoff et al (Proc. Natl. Acad. Sci. USA 1982 vol. 79 p. 1979 (Year: 1982).*
Wu et al. (Journal of Molecular Biology, 1999, vol. 294, pp. 151-162) (Year: 1999).*
Brodeur et al. (Can. J. Infect Dis 1992 vol. 3,p. 319-320). (Year: 1992).*
Mirkov et al. (Med Mycology 2012vol. 50, p. 476-487). (Year: 2012).*
Bloom, Barry R., et al., Mechanism of a Reaction in Vitro Associated with Delayed-Type Hypersensitivity, Journal Article, Jul. 1, 1966, pp. 80-82, vol. 153, Issue 3731, Science, US.
David, John R., et al., Delayed hypersensitivity in vitro: its mediation by cell-free substances formed by lymphoid cell-antigen interaction, Journal Article, Jul. 1, 1966, pp. 72-77, Vo. 56, Issue 1, PNAS, US.
Weiser, W Y, et al., Molecular cloning of a cDNA encoding a human macrophage migration inhibitory factor, Journal Article, Oct. 1, 1989, pp. 7522-7526, vol. 86, Issue 19, PNAS, US.
Sun, H W, et al., Crystal structure at 2.6—A resolution of human macrophage migration inhibitory factor, Journal Article, May 28, 1996, pp. 5191-5196, vol. 93, Issue 11, PNAS, US.
Calandra, Thierry, et al., MIF as a glucocorticoid-induced modulator of cytokine production, Journal Article, Sep. 7, 1995, pp. 377, 68-71, vol. 377, Issue 6544, Nature, US.
Baugh, John A., et al., Macrophage migration inhibitory factor, Journal Article, Jan. 2002, pp. S27-S35, vol. 30, Issue 1, Critical Care Medicine, US.
Mitchell, Robert A., Mechanisms and effectors of MIF-dependent promotion of tumourigenesis, Journal Article, Jan. 16, 2004, pp. 13-19, vol. 16, Issue 1, Cellular Signalling, US.
Lue, H., Macrophage migration inhibitory factor (MIF) promotes cell survival by activation of the Akt pathway and role for CSN5/JAB1 in the control of autocrine MIF activity, Journal Article, Feb. 19, 2007, pp. 5046-5059, vol. 26, Issue 35, Oncogene, US.
Nishihira, J., et al., Macrophage migration inhibitory factor (MIF): its essential role in the immune system and cell growth, Journal Article, Jul. 7, 2004, pp. 751-762, vol. 20, Issue 9, Journal of Interferon & Cytokine Research, US.
Shimizu et al., Identification of macrophage migration inhibitory factor (MIF) in human skin and its immunohistochemical localization., FEBS Lett. 1996; 381, 199-202.
Kawaguchi et al, A monoclonal antibody against migration inhibitory factor (MIF) obtained by immunization with MIF from the human lymphoblast cell line Mo, Leukoc. Biol. 1986, 39, 223-232.
Weiser et al., Generation of human hybridomas producing migration inhibitory factor (MIF) and of murine hybridomas secreting monoclonal antibodies to human MIF., Cell. Immunol. 1985, 90, 167-78.

(Continued)

*Primary Examiner* — Changhwa J Cheu
(74) *Attorney, Agent, or Firm* — Morgan Lewis & Bockius LLP

(57) ABSTRACT

The present invention pertains to the specific detection of MIF, in particular oxMIF, and of anti-oxMIF antibodies in tissues. A detection method is provided which uses immunohistochemistry or immunofluorescence and wherein specific anti-oxMIF antibodies and specific idiotypic monoclonal rabbit antibodies are used.

Figure 1A:
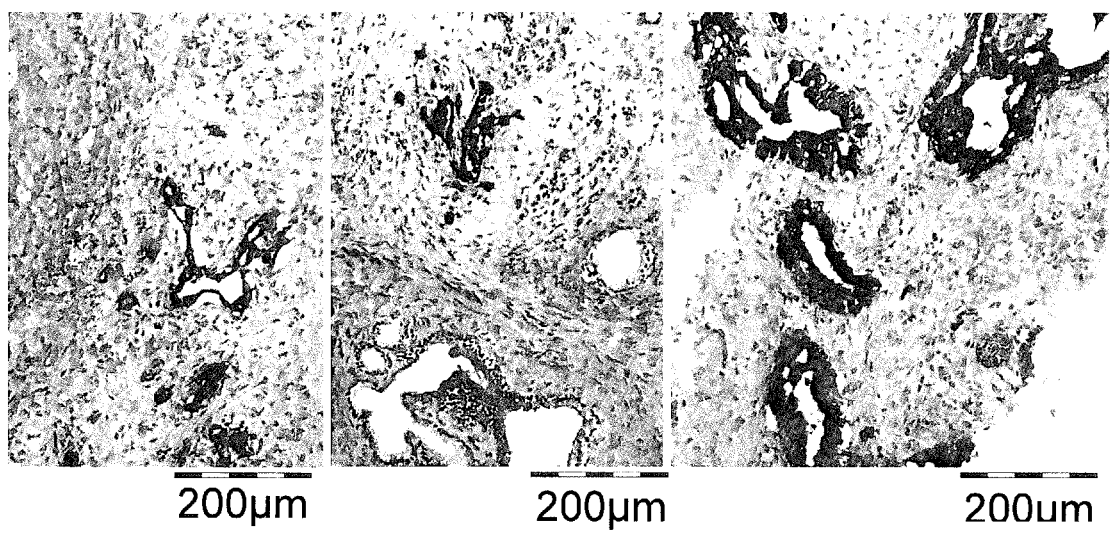

14 Claims, 12 Drawing Sheets
Specification includes a Sequence Listing.

(56) References Cited

OTHER PUBLICATIONS

Calandra et al., Macrophage migration inhibitory factor: a counter-regulator of glucocorticoid action and critical mediator of septic shock. (J. Inflamm. (1995), 47, 39-51.

Galat et al. A diversified family of 12-kDa proteins with a high amino acid sequence similarity to macrophage migration-inhibitory factor (MIF) (Eur. J. Biochem, 1994, 224, 417-21).

Watarai et al. Posttranslational modification of the glycosylation inhibiting factor (GIF) gene product generates bioactive GIF., (PNAS 2000, 97, 13251-6).

F. Hussain et al, "Human Anti-Macrophage Migration Inhibitory Factor Antibodies Inhibit Growth of Human Prostate Cancer Cells In Vitro and In Vivo", Molecular Cancer Therapeutics, (Jul. 1, 2013), vol. 12, No. 7, doi:10.1158/1535-7163.MCT-12-0988, ISSN 1535-7163, pp. 1223-1234.

R. J. Kerschbaumer et al, "Neutralization of Macrophage Migration Inhibitory Factor (MIF) by Fully Human Antibodies Correlates with Their Specificity for the—Sheet Structure of MIF", Journal of Biological Chemistry, (Jan. 11, 2012), vol. 287, No. 10, doi:10.1074/jbc.M111.329664, ISSN 0021-9258, pp. 7446-7455.

A. Schober et al, "Stabilization of Atherosclerotic Plaques by Blockade of Macrophage Migration Inhibitory Factor After Vascular Injury in Apolipoprotein E-Deficient Mice", Circulation, (Jan. 1, 2004), vol. 109, No. 3, doi:10.1161/01.CIR.0000109201.72441.09, ISSN 0009-7322, pp. 380-385.

Thiele et al, "Fully human antibodies specific for oxidized macrophage migration inhibitory factor (oxMIF) exhibit anti cancer activity in animal models", EARC-23 Poster Sessions / European Journal of Cancer, (Jul. 1, 2014), vol. 50, No. Suppl 5, doi:10.1016/S0959-8049(14)50714-9, pp. S95-S96.

Michael Thiele et al, "Abstract A181: Oxidized macrophage migration inhibitory factor (oxMIF) is a previously unrecognized, disease-related isoform of MIF and a potential new drug target in cancer.", Molecular Cancer Therapeutics, Proceedings of the AACR-NCI-EORTC International Conference: Molecular Targets and Cancer Therapeutics; Oct. 19-23, 2013; Boston, MA. Philadelphia, (Oct. 19, 2013), vol. 12, No. Suppl 11, doi:10.1158/1535-7163.TARG-13-A181, XP002741700 [I] 1-19 * abstract *.

* cited by examiner

200μm

200μm

Figure 3

| Clone Nr. | RAM9 | human IgG | Factor |
|---|---|---|---|
| 1 | 1.12 | 0.92 | 1.2 |
| 2 | 2.53 | 1.00 | 2.5 |
| 3 | 2.20 | 1.96 | 1.1 |
| 4 | 1.35 | 1.24 | 1.1 |
| 5 | 2.81 | 0.01 | 234.1 |
| 6 | 4.13 | 3.90 | 1.1 |
| 37 | 2.14 | 1.90 | 1.1 |
| 38 | 3.09 | 0.02 | 140.5 |
| 42 | 0.83 | 0.65 | 1.3 |
| 43 | 2.65 | 3.23 | 0.8 |
| 47 | 2.36 | 2.93 | 0.8 |
| 48 | 2.99 | 3.54 | 0.8 |
| 49 | 1.57 | 1.70 | 0.9 |
| 51 | 2.78 | 2.27 | 1.2 |
| 52 | 0.93 | -0.02 | 61.8 |
| 54 | 2.88 | 0.00 | 961.3 |
| 55 | 3.85 | 3.78 | 1.0 |
| 56 | 3.86 | 4.02 | 1.0 |
| 58 | 1.04 | 1.01 | 1.0 |
| 58 | 0.30 | 0.59 | 0.5 |
| 64 | 1.46 | 1.37 | 1.1 |
| 65 | 4.02 | 3.98 | 1.0 |
| 66 | 0.28 | 0.12 | 2.3 |
| 67 | 3.78 | 3.75 | 1.0 |
| 68 | 3.58 | 0.01 | 255.6 |
| 74 | 1.89 | 1.51 | 1.3 |

* Klone number 3 was included as a negative control as it did not pass the primary screening ELISA

ANTI-MIF IMMUNOHISTOCHEMISTRY

CROSS-REFERENCE TO RELATED APPLICATIONS

This application is a 371 National Phase of International Application No. PCT/EP2015/050005 filed Jan. 2, 2015, which claims the benefit of U.S. Provisional Application No. 61/923,464, filed Jan. 3, 2015, the disclosures for which are incorporated in its entirety.

The present invention pertains to the specific detection of MIF, in particular oxMIF, in tissues. The present detection method also allows the detection of anti-MIF antibodies, e.g. RAM9, in tissue. A detection method is provided which uses immunohistochemistry or immunofluorescence and wherein specific anti-oxMIF antibodies and monoclonal rabbit anti-oxMIF-antibody antibodies are used. The invention also provides advantageous detection antibodies and a method to provide such detection antibodies. The invention furthermore pertains to a method for the determination of target saturation.

BACKGROUND

Macrophage migration inhibitory factor (MIF) is a cytokine initially isolated based upon its ability to inhibit the in vitro random migration of peritoneal exudate cells from tuberculin hypersensitive guinea pigs (containing macrophages) (Bloom et al. Science 1966, 153, 80-2; David et al, PNAS 1966, 56, 72-7). Today, MIF is known as a critical upstream regulator of the innate and acquired immune response that exerts a pleiotropic spectrum of activities.

The human MIF-cDNA was cloned in 1989 (Weiser et al., PNAS 1989, 86, 7522-6), and its genomic localization was mapped to chromosome 22. The product of the human MIF gene is a protein with 114 amino acids (after cleavage of the N-terminal methionine) and an apparent molecular mass of about 12.5 kDa. MIF has no significant sequence homology to any other protein. The protein crystallizes as a trimer of identical subunits. Each monomer contains two antiparallel alpha-helices that pack against a four-stranded beta-sheet. The monomer has additional two beta-strands that interact with the beta-sheets of adjacent subunits to form the interface between monomers. The three subunits are arranged to form a barrel containing a solvent-accessible channel that runs through the centre of the protein along a molecular three-fold axis (Sun et al. PNAS 1996, 93, 5191-5196).

It was reported that MIF secretion from macrophages was induced at very low concentrations of glucocorticoids (Calandra et al. Nature 1995, 377, 68-71). However, MIF also counter-regulates the effects of glucocorticoids and stimulates the secretion of other cytokines such as tumor necrosis factor TNF-α and interleukin IL-1 β (Baugh et al., Crit Care Med 2002, 30, S27-35). MIF was also shown e.g. to exhibit pro-angiogenic, pro-proliferative and anti-apoptotic properties, thereby promoting tumor cell growth (Mitchell, R. A., Cellular Signalling, 2004. 16(1): p. 13-19; Lue, H. et al., Oncogene 2007. 26(35): p. 5046-59). It is also e.g. directly associated with the growth of lymphoma, melanoma, and colon cancer (Nishihira et al. J Interferon Cytokine Res, 2000, 20:751-62). MIF is a mediator of many pathologic conditions and thus associated with a variety of diseases including inter alia inflammatory bowel disease (IBD), rheumatoid arthritis (RA), acute respiratory distress syndrome (ARDS), asthma, glomerulonephritis, IgA nephropathy, myocardial infarction (MI), sepsis and cancer, though not limited thereto.

Polyclonal and monoclonal anti-MIF antibodies have been developed against recombinant human MIF (Shimizu et al., FEBS Lett. 1996; 381, 199-202; Kawaguchi et al, Leukoc. Biol. 1986, 39, 223-232, and Weiser et al., Cell. Immunol. 1985, 90, 167-78).

Anti-MIF antibodies have been suggested for therapeutic use. Calandra et al., (J. Inflamm. (1995), 47, 39-51) reportedly used anti-MIF antibodies to protect animals from experimentally induced gram-negative and gram-positive septic shock. Anti-MIF antibodies were suggested as a means of therapy to modulate cytokine production in septic shock and other inflammatory disease states.

U.S. Pat. No. 6,645,493 discloses monoclonal anti-MIF antibodies derived from hybridoma cells, which neutralize the biological activity of MIF. It could be shown in an animal model that these mouse-derived anti-MIF antibodies had a beneficial effect in the treatment of endotoxin-induced shock.

US 200310235584 discloses methods of preparing high affinity antibodies to MIF in animals in which the MIF gene has been homozygously knocked-out.

Glycosylation-inhibiting factor (GIF) is a protein described by Galat et al. (Eur. J. Biochem, 1994, 224, 417-21). MIF and GIF are now recognized to be identical. Watarai et al. (PNAS 2000, 97, 13251-6) described polyclonal antibodies binding to different GIF epitopes to identify the biochemical nature of the posttranslational modification of GIF in Is cells. Watarai et al, supra, reported that GIF occurs in different conformational isoforms in vitro. One type of isomer occurs by chemical modification of a single cysteine residue. The chemical modification leads to conformational changes within the GIF protein.

Elevated MIF levels—i.e., levels of MIF in general—are detected after the onset of various diseases, inter alia after the onset of inflammatory diseases or cancer. However, MIF circulates also in healthy subjects, which makes a clear differentiation difficult, oxMIF, on the contrary, is not present in healthy subjects. oxMIF is increased in disease states and detectable in samples of patients, like e.g. blood, serum and urine.

It has been discovered after thorough research of MIF and antibodies thereto that the antibodies RAB9, RAB4 and RAB0 specifically bind to oxMIF (and are incapable of binding to redMIF).

In earlier experiments carried out by the inventors, it could be shown that oxidative procedures like cystine-mediated oxidation, GSSG (ox. Glutathione)-mediated oxidation or incubation of MIF with Proclin300 or protein crosslinkers (e.g. BMOE) causes binding of MIF to the above-mentioned antibodies.

The surprising conclusions reached by the present inventors are:
  Redox modulation (Cystine/GSSG-mediated mild oxidation) of recombinant MIF (human, murine, rat, CHO, monkey)) or treatment of recombinant MIF with Proclin300 or protein crosslinkers leads to the binding of Baxter's anti-MIF antibodies RAB9, RAB4 and RAB0
  Reduction of oxMIF leads to the loss of Ab binding
  Specificity for oxMIF-isoforms correlates with biological Ab efficacy in vivo.
  oxMIF levels can be correlated with a disease state.

This additional knowledge regarding (ox)MIF served as a basis for the further studies of the present inventors.

It has been shown that the MIF protein exists in different isoforms. The specific detection of native occurring oxMIF, which is considered a strong and reliable marker for MIF related disease states, in tissues, like e.g. tissue sections on glass slides) by immunohistochemistry (in the following also IHC) or immunofluorescence (IF) approaches is hindered by the fact that the structure of oxMIF is influenced or frequently completely lost when standard IHC or IF approaches are applied. In some IHC or IF approaches, there is also a high background noise in tissues with endogenous biotin or avidin binding proteins and endogenous peroxidases.

Thus, there is a clear need for a reliable detection method for the oxMIF isoform. This need has been addressed by the present inventors and the goal has been achieved by the invention as described in the following. In particular, the invention described below is capable of highly sensitive and specific detection of oxMIF as well as anti-oxMIF antibodies in tissues with low background noise. Also, it is possible to carry out this method even in tissues of patients which were already treated with anti-oxMIF antibodies.

SUMMARY OF THE INVENTION

The present invention is directed to a detection method for the detection of oxMIF (ox macrophage migration inhibitory factor). The invention is also directed to the detection of anti-oxMIF antibodies. The detection method is based on the principle of an immunohistochemical detection. It is used on tissue samples, in particular tissue sections.

Preferably, these tissue sections are provided on a glass or plastic carrier, e.g. a glass or plastic slide.

The method uses specific oxMIF binding antibodies ("oxMIF binders", anti-oxMIF antibodies or primary antibodies; these expressions are used interchangeably throughout this application) and specific idiotypic anti-oxMIF binder antibodies ("idiotypic antibodies" or secondary antibodies; these expressions are used interchangeably throughout this application).

Preferred antibodies for use as oxMIF binders in the present invention are monoclonal antibodies. In a particularly preferred embodiment, the monoclonal anti-oxMIF antibodies are selected from the group consisting of RAB9, RAB0 and/or RAB4, or from the group consisting of RAM9, RAM0 and/or RAM4, as described in more detail below.

Furthermore, the present invention is particularly advantageous, as the inventors were successful in identifying idiotypic monoclonal antibodies directed against the above oxMIF binding antibodies which could reliably and specifically detect these oxMIF binding antibodies which are bound to oxMIF, Thus, the invention—in one embodiment—is directed to antibodies which are idiotypic for the herein described primary antibodies, They also bind specifically to these primary antibodies. Preferably, they bind specifically to these primary antibodies, when the primary antibodies are also bound to oxMIF. In a preferred embodiment, the idiotypic antibodies are rabbit idiotypic antibodies.

The most preferred secondary antibodies are those designated 54-5 and 68-1, both described in more detail below.

In a preferred embodiment, the invention provides a method for the provision of such secondary antibodies, wherein an immunization protocol with a Fab-fragment of an oxMIF antibody is performed, followed by a neutralizing ELISA screening. Antibodies are considered suitable as secondary antibodies if they have an $IC_{50}$ of ≤60 ng/ml in the neutralizing ELISA.

The advantageous specificity of the present method has been shown (see also example section below) by control stainings with isotype control antibodies (which are not able to detect MIF/oxMIF and are thus suitable as a negative control) or another anti-oxMIF monoclonal antibody (which is able to bind to oxMIF but cannot be detected by e.g. anti-RAM9 idiotypic antibody) and has been further verified by additional findings of the present inventors with the demonstration that oxMIF is detected only in diseased, e.g. cancerous tissue.

The detection method comprises in a preferred embodiment a staining step. This inventive detection/staining protocol itself was designed to conserve the native oxMIF structure in tissue sections. Standard techniques which had been known up to the present invention would lead to a conversion of MIF to oxMIF and would thus give false positive staining in immunohistochemistry techniques.

DETAILED DESCRIPTION OF THE INVENTION

The present invention is, in part, described by the following items:

1. An immunohistochemistry (IHC) assay method for in vitro detection of oxMIF, wherein oxMIF is MIF which is differentially binding to antibody RAB4, RAB9 and/or RAB0, in a tissue sample of a subject, comprising the determination of the binding of a compound to oxMIF in said sample in vitro, wherein one or more of the following steps are carried out:
    a) Optional Blocking step with blocking buffer and
    b) Binding step with primary anti-oxMIF antibody without a previous fixation step with an organic or inorganic fixation agent, in particular either formaldehyde or acetone;
    c) Optionally fixation step;
    d) Incubation with secondary antibody, wherein the secondary antibody is an anti-idiotypic rabbit monoclonal antibody directed against an anti-oxMIF antibody; and/or
    e) detection of binding between the primary anti-oxMIF antibody and the secondary antibody.
2. The IHC assay of item 1 wherein no fixation is carried out with an organic or inorganic fixation agent, in particular either formaldehyde or acetone, before the first binding step b).
3. The HC assay of item 1 or 2, wherein the sample is air dried, preferably for about 30 min.
4. The IHC assay of any one or more of items 1-3, wherein the primary antibody is not labelled e.g. not biotinylated and/or is preferably comprised in a primary dilution buffer and/or wherein the primary antibody is incubated with the sample preferably for 45 to 90 minutes, more preferred for approximately 60 minutes. Alternatively, the incubation time of primary antibody with sample can be 30 to 90 minutes, more preferred approximately 30 minutes.
5. The IHC assay of any one or more of items 1-4, wherein a washing step is carried out after binding step b) to wash away excess antibody, and wherein optionally further washing steps are carried out after all further steps.
6. The IHC assay of any one or more of items 1-5, wherein the detection step e) comprises or consists of a staining step and/or wherein a further (counter)staining step is carried out after the detection step, which can include the use of a tertiary antibody.
7. The IHC assay of any one or more of items 1-6, wherein the (counter)-staining step is carried out with hematoxylin after step e).
8. The IHC assay of any one of the preceding items, wherein the binding between primary and secondary antibody is detected by fluorescence, preferably by use of a fluorophore labelled tertiary antibody directed against the secondary antibody.
9. The IHC assay of any one of items 1-8, wherein said secondary antibody is selected from the group consisting of an anti-RAM9 antibody, an anti-RAM4 antibody and is most preferred an anti-RAM9 antibody, even more preferred a rabbit anti-RAM9 antibody.
10. The IHC assay of any one of items 1-9, wherein the primary antibody binds to oxMIF, but does not bind to redMIF.
11. The IHC assay of item 10, wherein the differential binding is a binding to oxMIF which occurs with a $K_D$ value of less than 100 nM, preferably less than 50 nM, even more preferred less than 10 nM and a non-binding to redMIF which is characterized by a $K_D$ of more than 400 nM.
12. The IHC assay of any one of items 1 to 11, wherein the primary antibodies are selected from the group consisting of oxMIF binders, like e.g. antibodies RAB4, RAB9 and/or RAB0 and/or RAM4, RAM9 and/or RAM0.
13. The IHC assay of any of the preceding items, wherein the sample is a tissue biopsy, preferably a frozen tissue biopsy, preferably an OCT embedded section, or a core needle biopsy.
14. An idiotypic antibody, specifically binding to an anti-oxMIF antibody, preferably to an anti-RAM9 antibody.
15. The idiotypic antibody of item 14, wherein the antibody is characterized by an $IC_{50}$ of ≤60 ng/ml in a neutralizing ELISA with immobilized MIF and RAM9.
16. An idiotypic antibody, preferably according to item 14 or 15, e.g. for use in the method or kit of any one or more of the preceding items, which is characterized by SEQ ID NO: 15 and/or 16, or by SEQ ID NO: 17 and/or 18.
17. An anti-idiotypic antibody, e.g. for use in the method or kit of any one or more of the preceding items, which is characterized by a heavy chain which has been deposited at the DSMZ with deposit No. DSM 28180 and/or by a light chain, which has been deposited at the DSMZ with deposit No. DSM 28181; or which is characterized by a heavy chain which has been deposited at the DSMZ with deposit No. DSM 28182 and/or a light chain which has been deposited at the DSMZ with a deposit no. DSM 28183.
18. A method for the detection of anti-oxMIF antibodies, preferably RAM9, RAM0 or RAM4, with the use of an idiotypic monoclonal rabbit antibody directed against said anti-oxMIF antibodies, preferably as described in any one of items 14-17.
19. In a preferred embodiment, the detection method of item 18 above detects RAM 9.
20. An IHC assay kit, adapted to carry out the method according to any one or more of the preceding items and/or comprising one or more antibodies as defined in the items above.

The present inventors also provide in a further particularly preferred embodiments the following method:
21. A method for the determination of target saturation of a target tissue with an anti-MIF antibody (preferably as defined in the items 1 and 10 to 12 above), wherein the target saturation is determined by the method as described in any one of items 1-13 above.

This method for the determination of target saturation is suitable to determine whether and how much anti-MIF antibody has actually reached the target tissue after administration of said anti-MIF antibody.

This method is also, in a particularly preferred embodiment, suitable to determine differences in target tissue saturation, e.g. between stoma and tumor cells.

One possible example for such a method is shown hereinbelow in Example 5 and FIG. 6 subsequent.

The above mentioned (primary) antibodies ("oxMIF binders") are characterized and supported by both their sequences as well as by deposits as plasmids in *E.coli* (strain TG1), comprising either the light or the heavy chain of each of the above mentioned antibodies RAB0, RAB4 and RAB9, respectively, as well as of RAM0, RAM4 and RAM9, respectively.

The plasmids are characterized by their DSM number which is the official number as obtained upon deposit under the Budapest Treaty with the German Collection of Microorganisms and Cell Cultures (DSMZ), Mascheroder Weg 1b, Braunschweig, Germany. The plasmids were deposited in *E. coli* strains, respectively.

The plasmid with the DSM 25110 number comprises the light chain sequence of the anti-MIF antibody RAB4.

The plasmid with the DSM 25112 number comprises the heavy chain (IgG4) sequence of the anti-MIF antibody RAB4.

The co-expression of plasmids DSM 25110 and DSM 25112 in a suitable host cell results in the production of preferred anti-MIF antibody RAB4.

The plasmid with the DSM 25111 number comprises the light chain sequence of the anti-MIF antibody RAB9.

The plasmid with the DSM 25113 number comprises the heavy chain (IgG4) sequence of the anti-MIF antibody RAB9.

The co-expression of plasmids DSM 25111 and DSM 25113 in a suitable host cell results in the production of preferred anti-MIF antibody RAB9.

The plasmid with the DSM 25114 number comprises the light chain sequence of the anti-MIF antibody RAB0.

The plasmid with the DSM 25115 number comprises the heavy chain (IgG4) sequence of the anti-MIF antibody RAB0.

The co-expression of plasmids DSM 25114 and DSM 25115 in a suitable host cell results in the production of preferred anti-MIF antibody RAB0.

Also deposited are antibodies RAM0, RAM9 and RAM4; all have been deposited with the DSZM, Braunschweig, Germany on Apr. 12, 2012 according to the Budapest Treaty, with the following designations:
RAM9—heavy chain: *E. coli* GA.662-01.pRAM9hc—DSM 25860.
RAM4—light chain: *E. coli* GA.906-04.pRAM4lc—DSM 25861.
RAM9—light chain: *E. coli* GA.661-01.pRAM9lc—DSM 25859.
RAM4—heavy chain: *E. coli* GA.657-02.pRAM4hc—DSM 25862.
RAM0—light chain: *E. coli* GA.906-01.pRAM0lc—DSM 25863.
RAM0—heavy chain: *E. coli* GA.784-01.pRAM0hc—DSM 25864.

Also deposited are antibodies 54-5, and 68-1; they have been deposited with the DSZM, Braunschweig, Germany on Dec. 19, 2013 according to the Budapest Treaty, with the following designations:
54-5—heavy chain: as *E.coli* TG1 anti-RAM9 antibody—DSM 28180.

54-5—light chain: as *E.coli* TG1 anti-RAM9 antibody—DSM 28181.
68-1—light chain: as *E.coli* TG1 anti-RAM9 antibody—DSM 28183.
68-1—heavy chain: as *E.coli* TG1 anti-RAM9 antibody—DSM 28182.

A biological sample in the context of this application in a preferred embodiment, is a tissue sample, preferably a tissue biopsy, a cryo-section of a tissue biopsy (freshly frozen or e.g. OCT embedded), or a core needle biopsy. However, in addition to the above mentioned preferred samples, all further known tissue or cell samples can be used in the present method, as known to a person skilled in the art. OCT embedding in this context refers to an embedding medium for embedding frozen tissue, which is a procedure amply used and well known in the art. OCT stands for Optimal Cutting Temperature, which is ensured by using e.g. this medium. An OCT medium will prevent the formation of freezing artefacts, e.g. destroyal of tissue by water. OCT medium is comprised of 10.24% polyvinyl alcohol, 4.26% polyethylene glycol and 85.50% non-reactive ingredient. This medium, or a similar medium according to general knowledge, is used to embed tissue before sectioning on an e.g. cryostat. Slight variations of this medium will have no influence on the present invention.

The detection of oxMIF in a sample from a patient is an important step for providing a reliable diagnosis of a disease or disorder, in particular to diagnose a patient with being afflicted with a MIF-related disease, i.e. a disease with a participation of (ox)MIF.

The term "prophylactic" or "therapeutic" treatment is art-recognized and refers to administration of a drug to a patient. If a given compound is administered prior to clinical manifestation of the unwanted condition (e.g. disease or other unwanted state of the host, e.g. a human or an animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects thereof).

As used herein an anti-(ox)MIF compound refers to any agent that attenuates, inhibits, opposes, counteracts, or decreases the biological activity of (ox)MIF. An anti(ox)MIF compound may be an agent that inhibits or neutralizes (ox)MIF activity, for example an antibody, particularly preferred, the antibodies as described herein, even more preferred the antibodies RAB9, RAB4 and/or RAB0, or RAM9, RAM4 and/or RAM0.

Figure 1B:
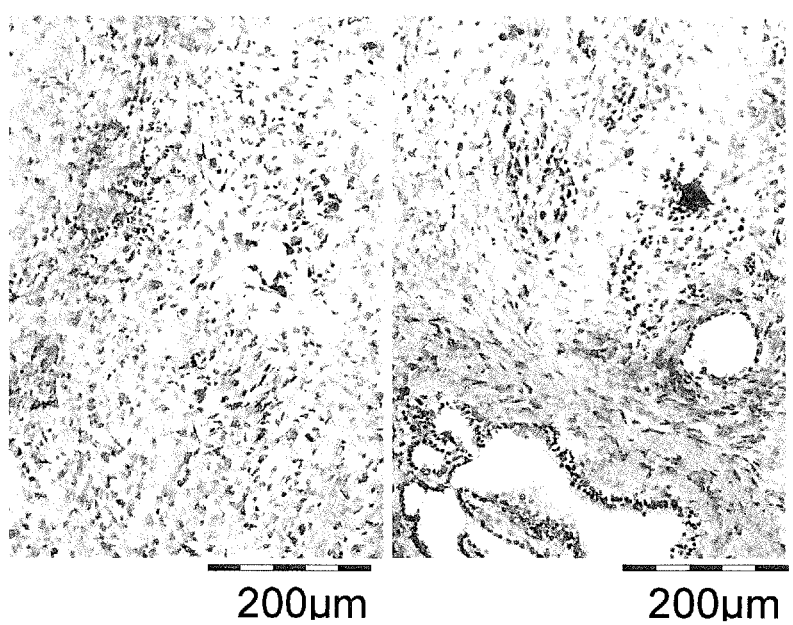

The present invention is further described by way of figures which are listed herein below:

FIG. 1A: in situ detection of oxMIF by immunohistochemistry in infiltrating ductal carcinoma of the pancreas, RAM9 primary antibody, plus rabbit anti-RAM9 (idiotypic, 68-1) as secondary antibody FIG. 1B: negative control for FIG. 1A

Figure 2A:
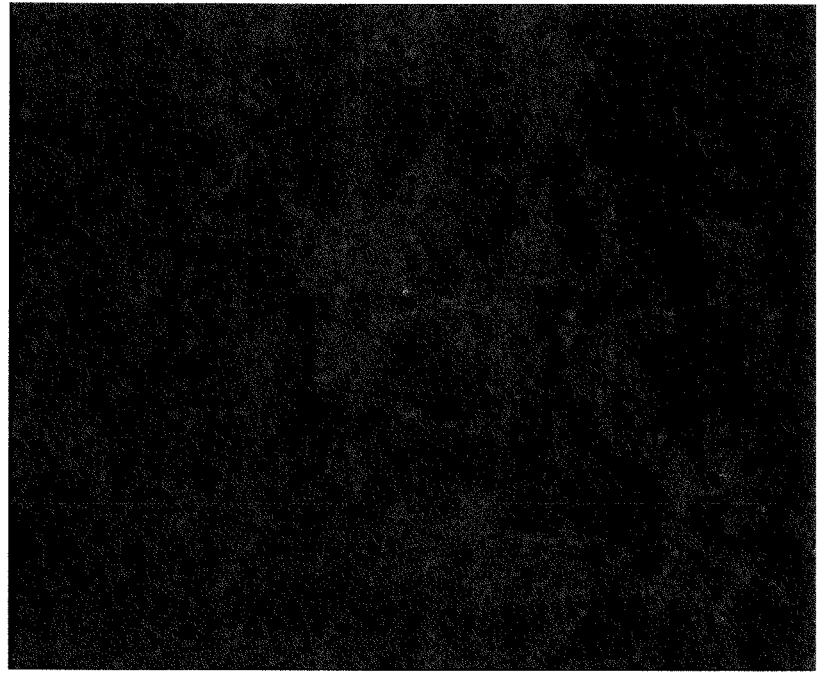

FIG. 2A: in situ detection of oxMIF by IHC in normal lung, primary antibody: RAM9, secondary antibody: rabbit anti-RAM9 (idiotypic)

Figure 2B:
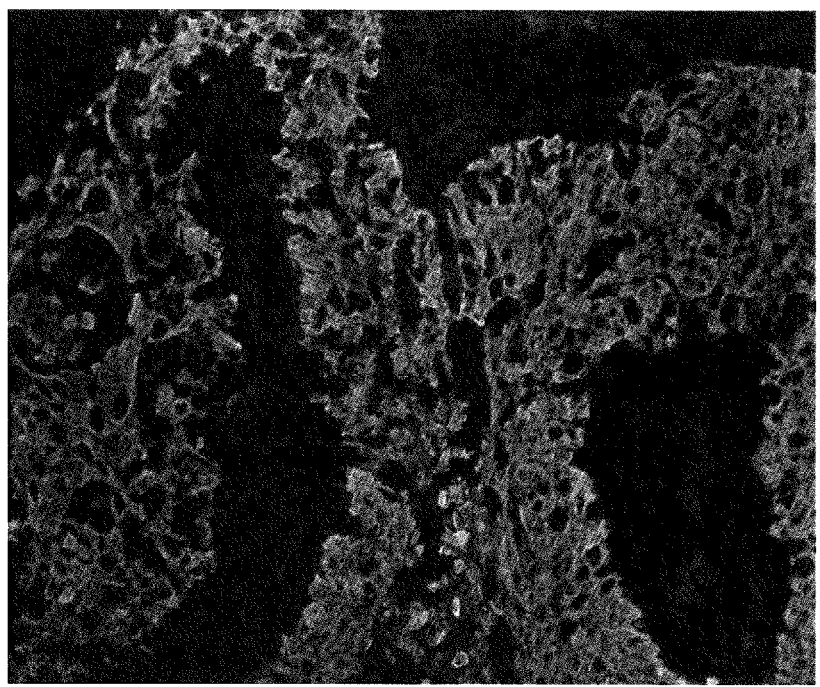

FIG. 2B: in situ detection of oxMIF by IHC in squamous cell carcinoma, primary antibody: RAM9, secondary antibody: rabbit anti-RAM9 (idiotypic)

FIG. 3: Primary Screening ELISA of monoclonal rabbit anti-RAM9 antibodies.

Figure 4A:
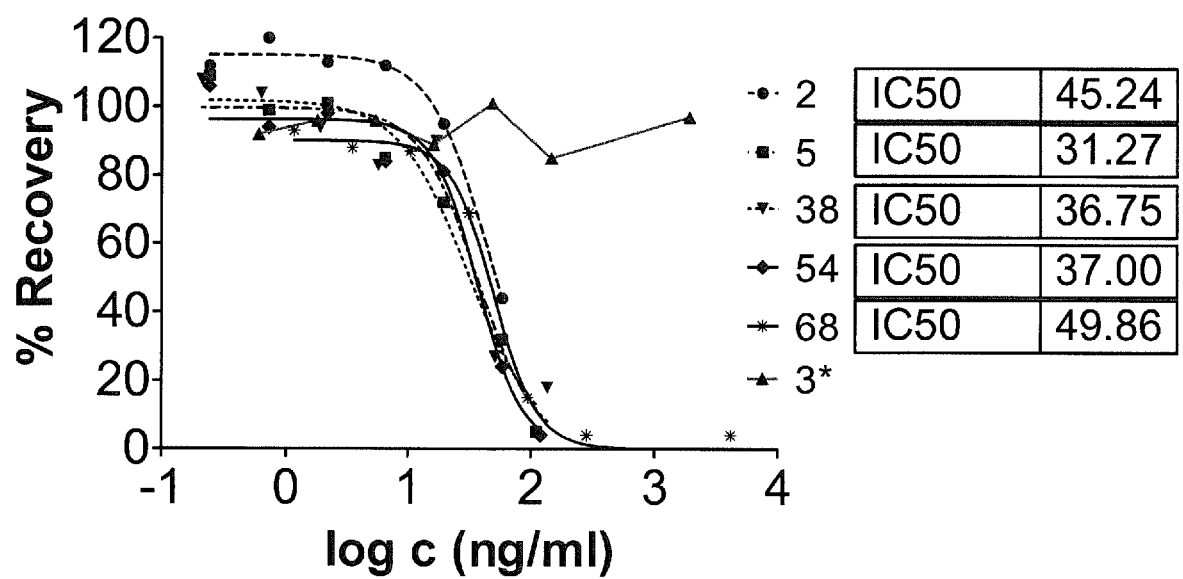

FIG. 4a: Secondary Screening ELISA of monoclonal rabbit anti-RAM9 antibodies.

Figure 4B:
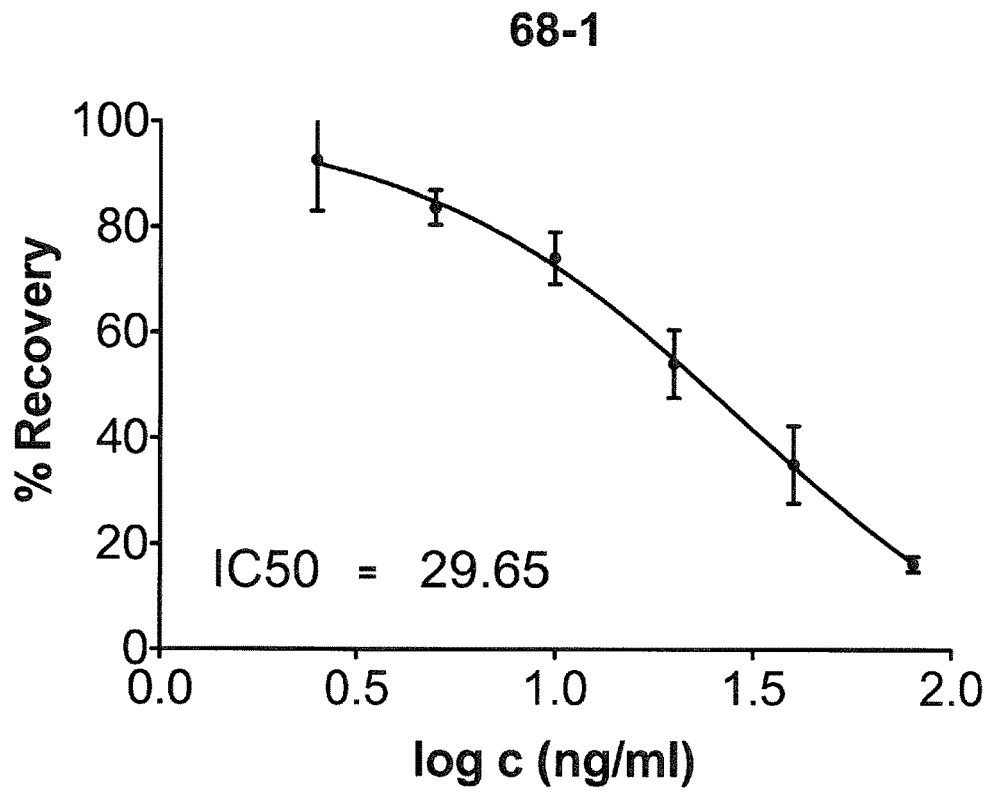
Figure 4B:
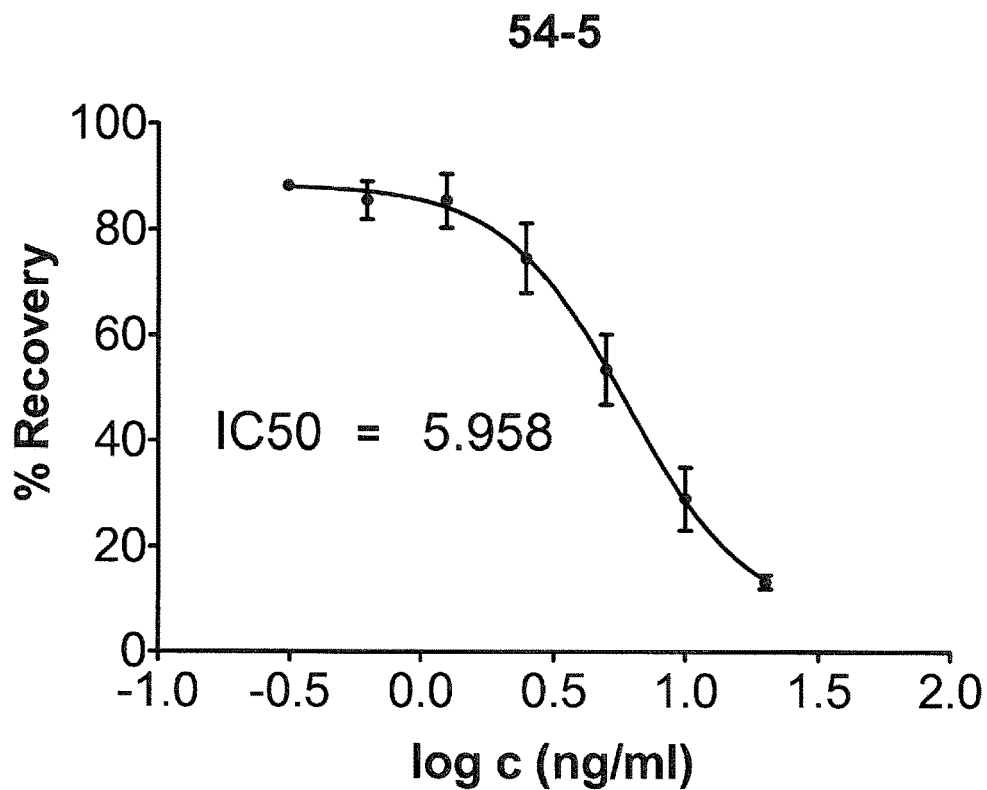

FIG. 4b: Secondary Screening ELISA of monoclonal rabbit anti-RAM9 antibodies 68-1 and 54-5, finally purified.

Figure 5:
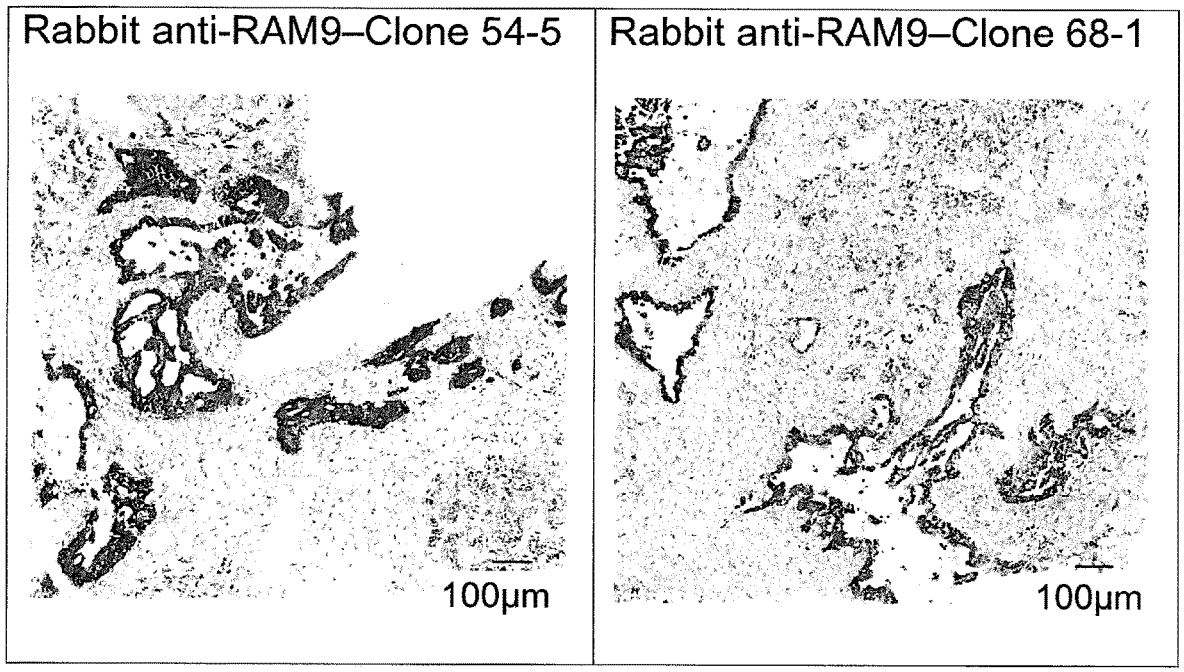
Figure 6:
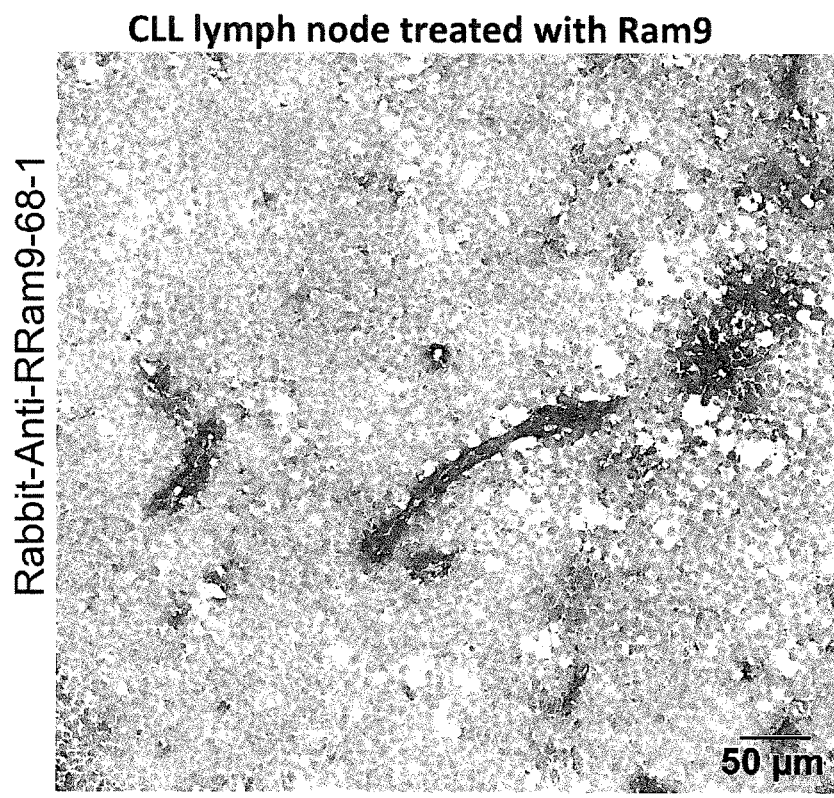
Figure 6:
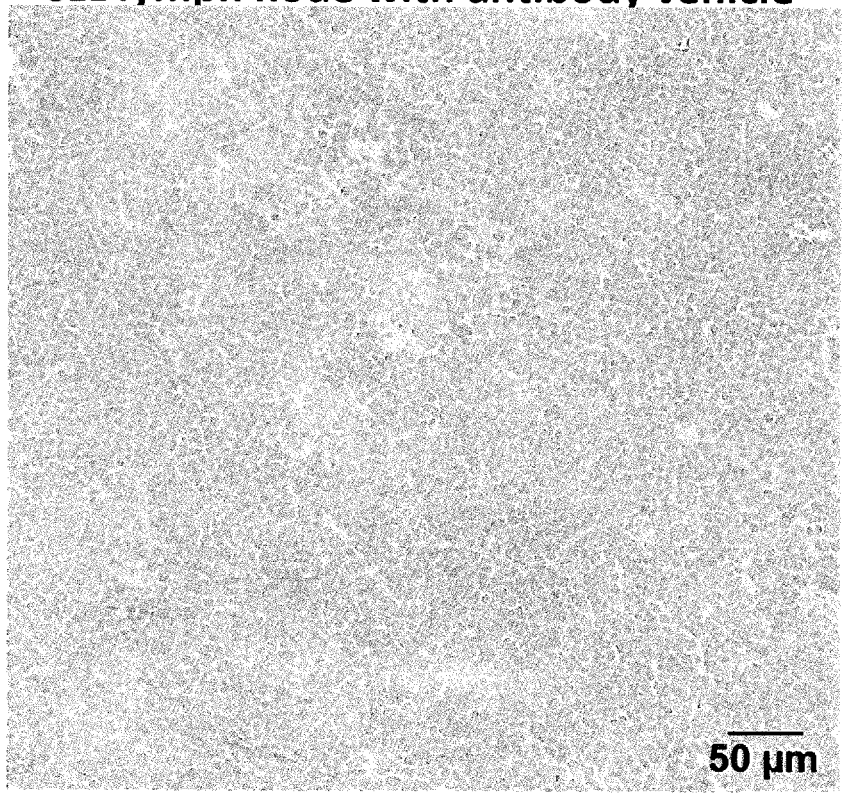
Figure 7:
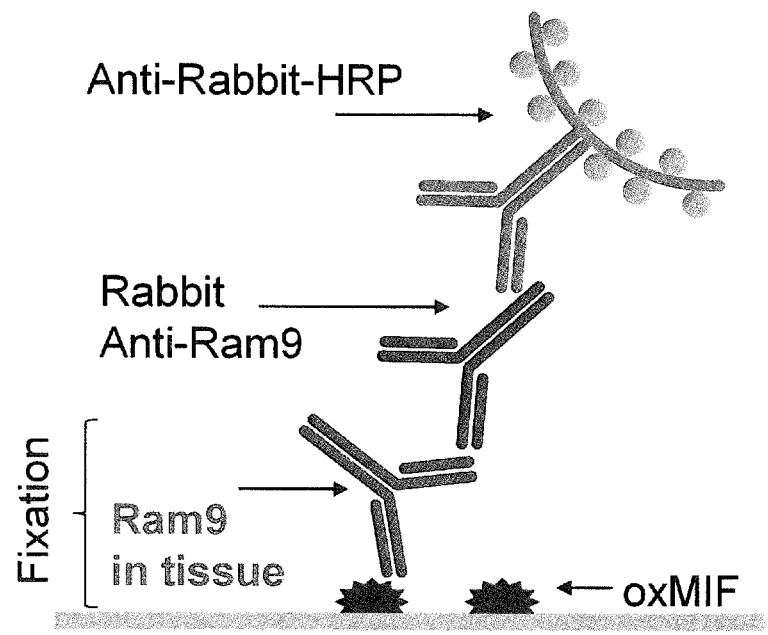
Figure 7:
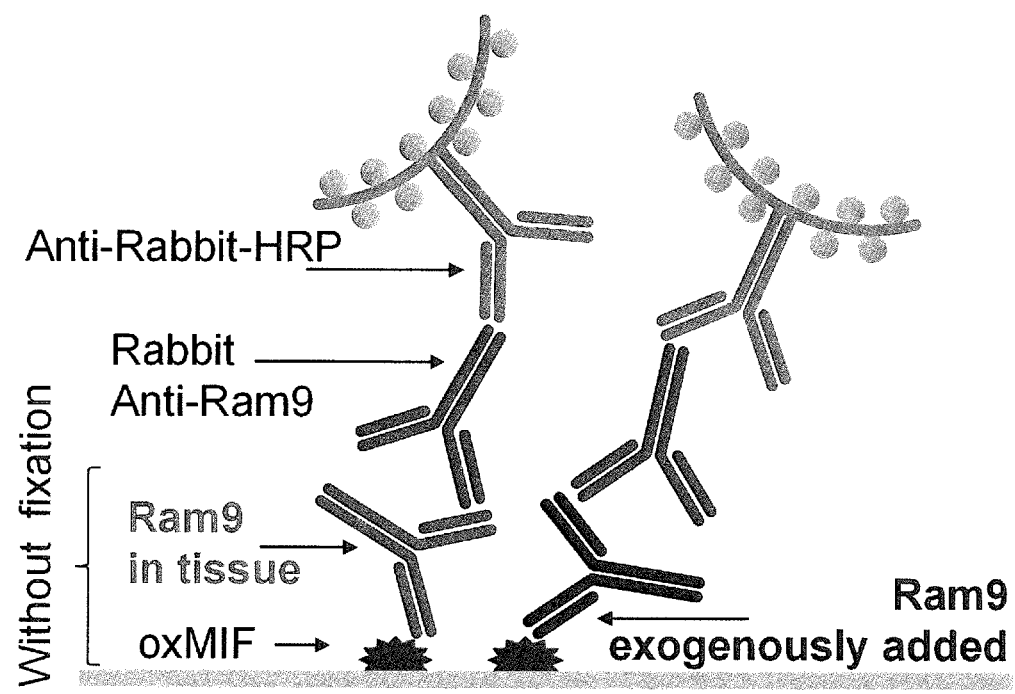

FIG. 5: in situ detection of oxMIF by immunohistochemistry in infiltrating ductal carcinoma of the pancreas, RAM9 primary antibody, plus rabbit anti-RAM9 (idiotypic), Clone 54-5 (left) and Clone 68-1 (right) as secondary antibody FIG. 6: Detection of anti-MIF antibody RAM9 in tissue FIG. 6a: CLL lymph node, RAM9 treated FIG. 6b: CLL lymph node, vehicle treated FIG. 7: Exemplary Figures and steps for target saturation calculation after immunohistochemistry of the present invention FIG. 8: Column 1 shows full slide scans of the CLL lymph node (see also example 5) tissue micro array. One lymph node per group and staining was selected to be shown in detail (black rectangle in first column, to be seen in second column). The calculation described in example 5 was however done on all lymph nodes. In the second column the dark gray mark up highlights the tissue area, that was annotated manually ($3^{rd}$ and $4^{th}$ picture from the top) or automatically by the software ($1^{st}$, and $2^{nd}$ picture from top). Light gray areas were excluded because of e.g. necrosis, tissue folding, etc. The third column shows representative original pictures from the annotated area in column 2 at higher magnification. The same representative pictures are shown in column 4 after automatic annotation of the brown chromogen (=marker area for RAM9 or oxMIF staining) by the software algorithm (dark gray to black areas). In the last column, the mean marker area of all lymph nodes is plotted in a bar chart for both RAM9 and oxMIF staining.

Figure 9:
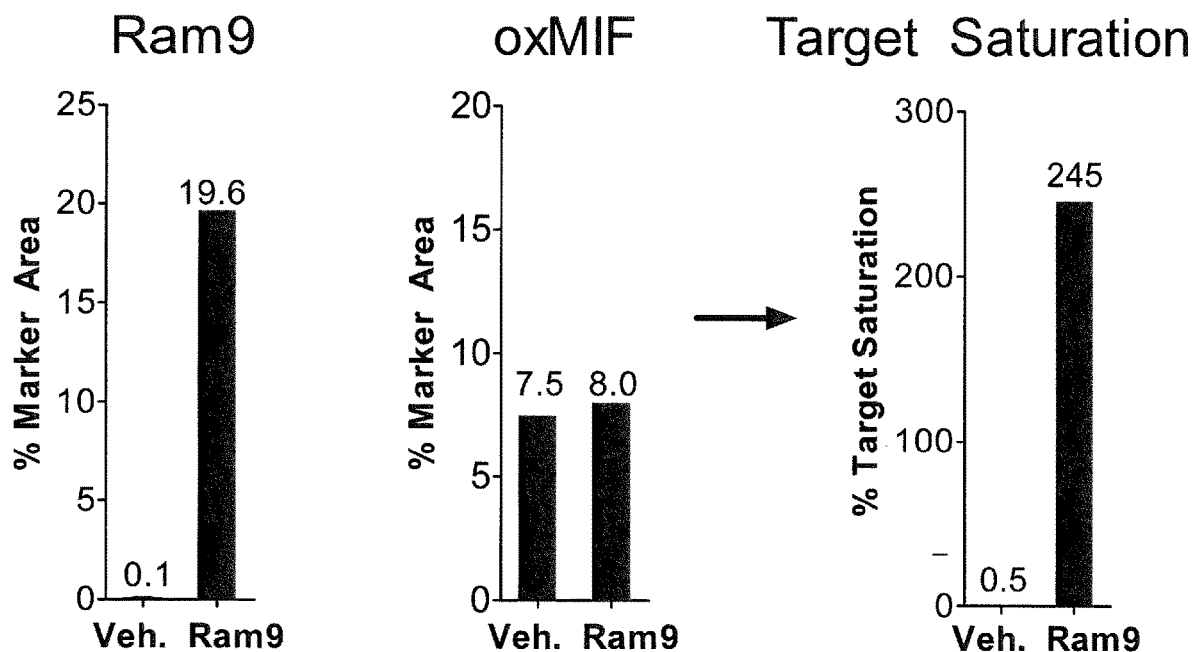

FIG. 9: Calculation of target saturation

Figure 10:
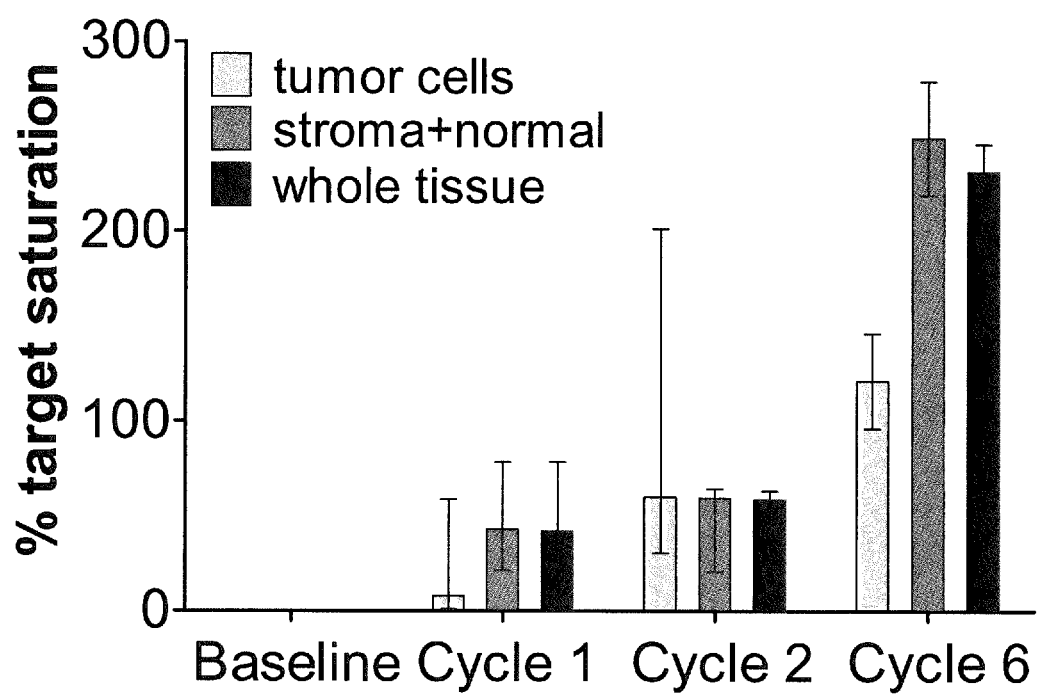

FIG. 10: Target saturation in tumor, in stroma and overall target saturation, Data indicate the median with interquartil-range

DEFINITIONS AND GENERAL TECHNIQUES

Unless otherwise defined herein, scientific and technical terms used in connection with the present invention shall have the meanings that are commonly understood by those of ordinary skill in the art. Generally, nomenclatures used in connection with, and techniques of, cell and tissue culture, molecular biology, immunology, microbiology, genetics and protein and nucleic acid chemistry described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al., Molecular Cloning: A Laboratory Manual, 2nd ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual, Cold Spring Harbor Laboratory Press, Cold Spring Harbor, N.Y. (1990), which are incorporated herein by reference.

"MIF" or "macrophage migration inhibitory factor" refers to the protein, which is known as a critical mediator in the immune and inflammatory response, and as a counterregulator of glucocorticoids. MIF includes mammalian MIF, specifically human MIF (Swiss-Prot primary accession number: P14174), wherein the monomeric form is encoded as a 115 amino acid protein but is produced as a 114 amino acid protein due to cleavage of the initial methionine.

"MIF" also includes "GIF" (glycosylation-inhibiting factor) and other forms of MIF such as fusion proteins of MIF. The numbering of the amino acids of MIF starts with the N-terminal methionine (amino acid 1) and ends with the C-terminal alanine (amino acid 115).

"oxidized MIF" or oxMIF is defined for the purposes of the invention as an isoform of MIF that occurs by treatment of MIF with mild oxidizing reagents, such as Cystine. As has been shown by the present invention, recombinant oxMIF that has been treated this way comprises isoform(s) of MIF that share structural rearrangements with oxMIF that (e.g.) occurs in vivo after challenge of animals with bacteria.

redMIF is defined for the purposes of this invention as reduced MIF and is MIF which does not bind to RAB0, RAB9 and/or RAB4.

The anti-oxMIF antibodies described in this invention are able to discriminate between ox and redMIF, which are generated by mild oxidation or reduction, respectively, and are useful to specifically detect oxMIF. Discrimination between these conformers is assessed by ELISA or surface plasmon resonance.

Assessing Differential Binding of the Antibodies by Biacore.

Binding kinetics of oxMIF and redMIF to antibody RAB9 and RAB0 are examined by surface plasmon resonance analysis using a Biacore 3000 System. The antibodies were coated on a CM5 (=carboxymethylated dextran) chip and recombinant MIF protein, pre-incubated with 0.2% Proclin300, were injected. (Proclin300 consists of oxidative isothiazolones that stabilize the oxMIF structure by avoiding a conversion of oxMIF to redMIF). In native HBS-EP buffer (=Biacore running buffer) without addition of ProClin300, none of the recombinant MIF proteins bound to RAB9, RAB0 or to the reference antibody (irrelevant isotype control antibody) used as negative (background) binding control.

In a preferred embodiment, oxMIF is MIF which is differentially bound by antibody RAB9, RAB4 and/or RAB0 or an antigen-binding fragment thereof, meaning that these antibodies do bind to oxMIF while redMIF is not bound by either one of these antibodies.

In other embodiments, the anti-oxMIF antibodies ("oxMIF binders"), e.g. the antibodies mentioned above or an antigen-binding portion thereof bind oxMIF with a $K_D$ of less than 100 nM, preferably a $K_D$ of Less than 50 nM, even more preferred with a $K_D$ of less than 10 nM. Particularly preferred, the antibodies of this invention bind to oxMIF with a $K_D$ of less than 5 nM.

(Non-)binding of an antibody, e.g. RAB9, RAB4 or RAB0 (to oxMIF or redMIF) can be determined as generally known to a person skilled in the art, examples being any one of the following methods: Differential Binding ELISA with recombinant MIF, or surface plasmon resonance using recombinant MIF in its reduced or oxidized state, like the well known Biacore assay, described above.

A preferred method for the determination of binding is surface plasmon resonance of an antibody to e.g. rec. (ox)MIF whereupon "binding" is meant to be represented by a $K_D$ of less than 100 nM preferably less than 50 nM, even more preferred less than 10 nM whereas the non-binding to redMIF is characterized by a $K_D$ of more than 400 nM. "Binding" and "specific binding" is used interchangeably here to denote the above. "Differential binding" in the context of this application means that a compound, in particular the antibodies as described herein, bind to oxMIF (e.g. with the $K_D$ values mentioned above) while they do not bind to redMIF (with non-binding again being defined as above).

An "antibody" refers to an intact antibody or an antigen-binding portion that competes with the intact antibody for (specific) binding. See generally, Fundamental Immunology, Ch. 7 (Paul, W., ed., 2nd ed. Raven Press, N.Y. (1989)) (incorporated by reference). The term antibody includes human antibodies, mammalian antibodies, isolated antibodies and genetically engineered forms such as chimeric, camelized or humanized antibodies, though not being limited thereto.

The term "antigen-binding portion" of an antibody refers to one or more fragments of an antibody that retain the ability to specifically bind to an antigen (e.g. (ox)MIF). Antigen-binding portions may be produced by recombinant DNA techniques or by enzymatic or chemical cleavage of intact antibodies. Antigen-binding portions include e.g.— though not limited thereto—the following: Fab, Fab', F(ab')2, Fv, and complementarity determining region (CDR) fragments, single-chain antibodies (scFv), chimeric antibodies, antibodies and polypeptides that contain at least a portion of an antibody that is sufficient to confer specific antigen binding to the polypeptide, i.e. ox or redMIF. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia et al. J. Mol. Biol. 196:901-917 (1987), or Chothia et al., Nature 342:878-883 (1989). An antibody or antigen-binding portion thereof can be derivatized or linked to another functional molecule (e.g., another peptide or protein). For example, an antibody or antigen-binding portion thereof can be functionally linked to one or more other molecular entities, such as another antibody (e.g., a bispecific antibody or a diabody), a detectable agent, a cytotoxic agent, a pharmaceutical agent, and/or a linking molecule.

The term "$K_D$" refers here, in accordance with the general knowledge of a person skilled in the art to the equilibrium dissociation constant of a particular antibody with the respective antigen. This equilibrium dissociation constant measures the propensity of a larger object (here: complex ox or red MIF/antibody) to separate, i.e. dissociate into smaller components (here: ox or redMIF and antibody).

The term "human antibody" refers to any antibody in which the variable and constant domains are human sequences. The term encompasses antibodies with sequences derived from human genes, but which have been changed, e.g. to decrease possible immunogenicity, increase affinity, eliminate cysteins that might cause undesirable folding, etc. The term encompasses such antibodies produced recombinantly in non-human cells, which might e.g. impart glycosylation not typical of human cells.

The term "humanized antibody" refers to antibodies comprising human sequences and containing also non-human sequences.

The term "camelized antibody" refers to antibodies wherein the antibody structure or sequences has been changed to more closely resemble antibodies from camels, also designated camelid antibodies. Methods for the design and production of camelized antibodies are part of the general knowledge of a person skilled in the art.

The term "chimeric antibody" refers to an antibody that comprises regions from two or more different species. The term "isolated antibody" or "isolated antigen-binding portion thereof" refers to an antibody or an antigen-binding portion thereof that has been identified and selected from an antibody source such as a phage display library or a B-cell repertoire.

The production of the anti-(ox)MIF antibodies ("oxMIF binders") according to the present invention includes any method for the generation of recombinant DNA by genetic engineering, e.g. via reverse transcription of RNA and/or amplification of DNA and cloning into expression vectors. In some embodiments, the vector is a viral vector, wherein additional DNA segments may be ligated into the viral genome. In some embodiments, the vector is capable of autonomous replication in a host cell into which it is introduced (e.g. bacterial vectors having a bacterial origin of replication and episomal mammalian vectors). In other embodiments, the vector (e.g. non-episomal mammalian vectors) can be integrated into the genome of a host cell upon introduction into the host cell, and thereby replicated along with the host genome. Moreover, certain vectors are capable of directing the expression of genes to which they are operatively linked. Such vectors are referred to herein as "recombinant expression vectors" (or simply, "expression vectors").

Anti-(ox)MIF antibodies ("oxMIF binders") can be produced inter alia by means of conventional expression vectors, such as bacterial vectors (e.g., pBR322 and its derivatives), or eukaryotic vectors. Those sequences that encode the antibody can be provided with regulatory sequences that regulate the replication, expression and/or secretion from the host cell. These regulatory sequences comprise, for instance, promoters (e.g., CMV or SV40) and signal sequences. The expression vectors can also comprise selection and amplification markers, such as the dihydrofolate reductase gene (DHFR), hygromycin-B-phosphotransferase, and thymidine-kinase. The components of the vectors used, such as selection markers, replicons, enhancers, can either be commercially obtained or prepared by means of conventional methods. The vectors can be constructed for the expression in various cell cultures, e.g., in mammalian cells such as CHO, COS, HEK293, NSO, fibroblasts, insect cells, yeast or bacteria such as *E.coli*. In some instances, cells are used that allow for optimal glycosylation of the expressed protein.

The anti-(ox)MIF antibody light chain gene(s) and the anti-(ox)MIF antibody heavy chain gene(s) can be inserted into separate vectors or the genes are inserted into the same expression vector. The antibody genes are inserted into the expression vector by standard methods, e.g., ligation of complementary restriction sites on the antibody gene fragment and vector, or blunt end ligation if no restriction sites are present.

The production of anti-(ox)MIF antibodies ("oxMIF binders") or antigen-binding fragments thereof may include any method known in the art for the introduction of recombinant DNA into eukaryotic cells by transfection, e.g. via electroporation or microinjection. For example, the recombinant expression of anti-(ox)MIF antibody can be achieved by introducing an expression plasmid containing the anti-(ox) MIF antibody encoding DNA sequence under the control of one or more regulating sequences such as a strong promoter, into a suitable host cell line, by an appropriate transfection method resulting in cells having the introduced sequences stably integrated into the genome. The lipofection method is an example of a transfection method which may be used according to the present invention.

The production of anti-(ox)MIF antibodies ("oxMIF binders") may also include any method known in the art for the cultivation of said transformed cells, e.g. in a continuous or batchwise manner, and the expression of the anti-(ox)MIF antibody, e.g. constitutive or upon induction. It is referred in particular to WO 2009/086920 for further reference for the production of anti-(ox)MIF antibodies. In a preferred embodiment, the anti-(ox)MIF antibodies as produced according to the present invention bind to oxMIF or an epitope thereof. Particularly preferred antibodies in accordance with the present invention are antibodies RAB9, RAB4 and/or RAB0 as well as RAM9, RAM4 and/or RAM0.

The sequences of these antibodies are partly also disclosed in WO 2009/086920; see in addition the sequence list of the present application and the following:

```
SEQ ID NO: 1 for the amino acid sequence of the
light chain of RAB9:
DIQMTQSPSS LSASVGDRVT ITCRSSQRIM TYLNWYQQKP

GKAPKLLIFV ASHSQSGVPS RFRGSGSETD FTLTISGLQP

EDSATYYCQQ SFWTPLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC,

SEQ ID NO: 2 for the amino acid sequence of the
light chain of RAB4:
DIQMTQSPGT LSLSPGERAT LSCRASQGVS SSSLAWYQQK

PGQAPRLLIY GTSSRATGIP DRFSGSASGT DFTLTISRLQ

PEDFAVYYCQ QYGRSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC,

SEQ ID NO: 3 for the amino acid sequence of the
light chain of RAB0:
DIQMTQSPGT LSLSPGERAT LSCRASQGVS SSSLAWYQQK

PGQAPRLLIY GTSSRATGIP DRFSGSASGT DFTLTISRLQ

PEDFAVYYCQ QYGRSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC,

SEQ ID NO: 4 for the amino acid sequence of the
light chain of RAB2:
DIQMTQSPVT LSLSPGERAT LSCRASQSVR SSYLAWYQQK

PGQTPRLLIY GASNRATGIP DRFSGSGSGT DFTLTISRLE

PEDFAVYYCQ QYGNSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC,

SEQ ID NO: 5 for the amino acid sequence of the
heavy chain of RAB9:
EVQLLESGGG LVQPGGSLRL SCAASGFTFS IYSMNWVRQA

PGKGLEWVSS IGSSGGTTYY ADSVKGRFTI SRDNSKNTLY

LQMNSLRAED TAVYYCAGSQ WLYGMDVWGQ GTTVTVSSAS

TKGPSVFPLA PCSRSTSEST AALGCLVKDY FPEPVTVSWN
```

-continued

SGALTSGVHT FPAVLQSSGL YSLSSVVTVP SSSLGTKTYT

CNVDHKPSNT KVDKRVESKY GPPCPPCPAP EFLGGPSVFL

FPPKPKDTLM ISRTPEVTCV VVDVSQEDPE VQFNWYVDGV

EVHNAKTKPR EEQFNSTYRV VSVLTVLHQD WLNGKEYKCK

VSNKGLPSSI EKTISKAKGQ PREPQVYTLP PSQEEMTKNQ

VSLTCLVKGF YPSDIAVEWE SNGQPENNYK TTPPVLDSDG

SFFLYSRLTV DKSRWQEGNV FSCSVMHEAL HNHYTQKSLS

LSLGK,

SEQ ID NO: 6 for the amino acid sequence of the
heavy chain of RAB4:
EVQLLESGGG LVQPGGSLRL SCAASGFTFS TYAMDWVRQA

PGKGLEWVSG IVPSGGFTKY ADSVKGRFTI SRDNSKNTLY

LQMNSLRAED TAVYYCARVN VIAVAGTGYY YYGMDVWGQG

TTVTVSSAST KGPSVFPLAP CSRSTSESTA ALGCLVKDYF

PEPVTVSWNS GALTSGVHTF PAVLQSSGLY SLSSVVTVPS

SSLGTKTYTC NVDHKPSNTK VDKRVESKYG PPCPPCPAPE

FLGGPSVFLF PPKPKDTLMI SRTPEVTCVV VDVSQEDPEV

QFNWYVDGVE VHNAKTKPRE EQFNSTYRVV SVLTVLHQDW

LNGKEYKCKV SNKGLPSSIE KTISKAKGQP REPQVYTLPP

SQEEMTKNQV SLTCLVKGFY PSDIAVEWES NGQPENNYKT

TPPVLDSDGS FFLYSRLTVD KSRWQEGNVF SCSVMHEALH

NHYTQKSLSL SLGK,

SEQ ID NO: 7 for the amino acid sequence of the
heavy chain of RAB0:
EVQLLESGGG LVQPGGSLRL SCAASGFTFS WYAMDWVRQA

PGKGLEWVSG IYPSGGRTKY ADSVKGRFTI SRDNSKNTLY

LQMNSLRAED TAVYYCARVN VIAVAGTGYY YYGMDVWGQG

TTVTVSSAST KGPSVFPLAP CSRSTSESTA ALGCLVKDYF

PEPVTVSWNS GALTSGVHTF PAVLQSSGLY SLSSVVTVPS

SSLGTKTYTC NVDHKPSNTK VDKRVESKYG PPCPPCPAPE

FLGGPSVFLF PPKPKDTLMI SRTPEVTCVV VDVSQEDPEV

QFNWYVDGVE VHNAKTKPRE EQFNSTYRVV SVLTVLHQDW

LNGKEYKCKV SNKGLPSSIE KTISKAKGQP REPQVYTLPP

SQEEMTKNQV SLTCLVKGFY PSDIAVEWES NGQPENNYKT

TPPVLDSDGS FFLYSRLTVD KSRWQEGNVF SCSVMHEALH

NHYTQKSLSL SLGK,

SEQ ID NO: 8 for the amino acid sequence of the
heavy chain of RAB2:
EVQLLESGGG LVQPGGSLRL SCAASGFTFS IYAMDWVRQA

PGKGLEWVSG IVPSGGFTKY ADSVKGRFTI SRDNSKNTLY

LQMNSLRAED TAVYYCARVN VIAVAGTGYY YYGMDVWGQG

TTVTVSSAST KGPSVFPLAP CSRSTSESTA ALGCLVKDYF

PEPVTVSWNS GALTSGVHTF PAVLQSSGLY SLSSVVTVPS

SSLGTKTYTC NVDHKPSNTK VDKRVESKYG PPCPPCPAPE

FLGGPSVFLF PPKPKDTLMI SRTPEVTCVV VDVSQEDPEV

QFNWYVDGVE VHNAKTKPRE EQFNSTYRVV SVLTVLHQDW

LNGKEYKCKV SNKGLPSSIE KTISKAKGQP REPQVYTLPP

SQEEMTKNQV SLTCLVKGFY PSDIAVEWES NGQPENNYKT

TPPVLDSDGS FFLYSRLTVD KSRWQEGNVF SCSVMHEALH

NHYTQKSLSL SLGK,

SEQ ID NO: 9 for the amino acid sequence of
RAM0hc:
EVQLLESGGG LVQPGGSLRL SCAASGFTFS WYAMDWVRQA

PGKGLEWVSG IYPSGGRTKY ADSVKGRFTI SRDNSKNTLY

LQMNSLRAED TAVYYCARVN VIAVAGTGYY YYGMDVWGQG

TTVTVSSAST KGPSVFPLAP SSKSTSGGTA ALGCLVKDYF

PEPVTVSWNS GALTSGVHTF PAVLQSSGLY SLSSVVTVPS

SSLGTQTYIC NVNHKPSNTK VDKRVEPKSC DKTHTCPPCP

APELLGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGK,

SEQ ID NO: 10 for the amino acid sequence of
RAM01c:
DIQMTQSPGT LSLSPGERAT LSCRASQGVS SSSLAWYQQK

PGQAPRLLIY GTSSRATGIP DRFSGSASGT DFTLTISRLQ

PEDFAVYYCQ QYGRSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC,

SEQ ID NO: 11 for the amino acid sequence of
RAM9hc:
EVQLLESGGG LVQPGGSLRL SCAASGFTFS IYSMNWVRQA

PGKGLEWVSS IGSSGGTTYY ADSVKGRFTI SRDNSKNTLY

LQMNSLRAED TAVYYCAGSQ WLYGMDVWGQ GTTVTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPELLGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLTCLV KGFYPSDIAV EWESNGQPEN NYKTTPPVLD

SDGSFFLYSK LTVDKSRWQQ GNVFSCSVMH EALHNHYTQK

SLSLSPGK,

SEQ ID NO: 12 for the amino acid sequence of
RAM91c:
DIQMTQSPSS LSASVGDRVT ITCRSSQRIM TYLNWYQQKP

GKAPKLLIFV ASHSQSGVPS RFRGSGSETD FTLTISGLQP

EDSATYYCQQ SFWTPLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC,

SEQ ID NO: 13 for the amino acid sequence of
RAM4hc:
EVQLLESGGG LVQPGGSLRL SCAASGFTFS IYAMDWVRQA

PGKGLEWVSG IVPSGGFTKY ADSVKGRFTI SRDNSKNTLY

LQMNSLRAED TAVYYCARVN VIAVAGTGYY YYGMDVWGQG

TTVTVSSAST KGPSVFPLAP SSKSTSGGTA ALGCLVKDYF

PEPVTVSWNS GALTSGVHTF PAVLQSSGLY SLSSVVTVPS

SSLGTQTYIC NVNHKPSNTK VDKRVEPKSC DKTHTCPPCP

APELLGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGK,

SEQ ID NO: 14 for the amino acid sequence of
RAM41c:
DIQMTQSPGT LSLSPGERAT LSCRASQGVS SSSLAWYQQK

PGQAPRLLIY GTSSRATGIP DRFSGSASGT DFTLTISRLQ

PEDFAVYYCQ QYGRSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC.

SEQ ID NO: 15 for the amino acid sequence of
anti-RAM9-68-1hc
Q EQLKESGGRL VKPGGTLTLT CKASGMDFNN YYYMAWVRQA

PGKGLEWIGY ISGGGSPYYA SWAKGRFTIS RTSTTVDLKM

TSLTTEDTAT YFCGRYTDIN NGIDLWGPGT LVTVSSGQPK

APSVFPLAPC CGDTPSSTVT LGCLVKGYLP EPVTVTWNSG

TLTNGVRTFP SVRQSSGLYS LSSVVSVTSS SQPVTCNVAH

PATNTKVDKT VAPSTCSKPT CPPPELLGGP SVFIFPPKPK

DTLMISRTPE VTCVVVDVSQ DDPEVQFTWY INNEQVRTAR

PPLREQQFNS TIRVVSTLPI AHQDWLRGKE FKCKVHNKAL

PAPIEKTISK ARGQPLEPKV YTMGPPREEL SSRSVSLTCM

INGFYPSDIS VEWEKNGKAE DNYKTTPAVL DSDGSYFLYS

KLSVPTSEWQ RGDVFTCSVM HEALHNHYTQ KSISRSPGK

SEQ ID NO: 16 for the amino acid sequence of
anti-RAM9-68-11c
DIVMTQT PSSVSEPVGG TVTINCQASE NIYSNLAWYQ

QKPGQPPKLL IYLASSLTSG VPSRFKGSGS GTEFTLTISD

LECADAAIYY CQNNYGDVRY GRNAFGGGTE VVVKGDPVAP

TVLIFPPAAD QVATGTVTIV CVANKYFPDV TVTWEVDGTT

QTTGIENSKT PQNSADCTYN LSSTLTLTST QYNSHKEYTC

KVTQGTTSVV QSFNRGDC

SEQ ID NO: 17 for the amino acid sequence of
anti-RAM9-54-5hc
Q SLEESGGDLV KPGASLTLTC TASGFSFSSG YDMCWVRQAP

GKGLEWIACI YDGDVRTYYA SWAKGRFTIS RTSSTTMTLQ

MTGLTAADTA TYLCARGASG YLSALYLWGP GTLVTVSSGQ

PKAPSVFPLA PCCGDTPSST VTLGCLVKGY LPEPVTVTWN

SGTLTNGVRT FPSVRQSSGL YSLSSVVSVT SSSQPVTCNV

AHPATNTKVD KTVAPSTCSK PTCPPPELLG GPSVFIFPPK

PKDTLMISRT PEVTCVVVDV SQDDPEVQFT WYINNEQVRT

ARPPLREQQF NSTIRVVSTL PIAHQDWLRG KEFKCKVHNK

ALPAPIEKTI SKARGQPLEP KVYTMGPPRE ELSSRSVSLT

CMINGFYPSD ISVEWEKNGK AEDNYKTTPA VLDSDGSYFL

YSKLSVPTSE WQRGDVFTCS VMHEALHNHY TQKSISRSPG K

SEQ ID NO: 18 for the amino acid sequence of
anti-RAM9-54-5lc
DVVMTQTP ASVSEPVGGT VTIKCQASFT ITSNLAWYQQ

KPGQPPKLLI YGASNLASGV SSRFRGSGFG TEFTLTISDL

ECADAATYYC QCAAVLSSWT FGGGTEVVVK GDPVAPTVLI

FPPAADQVAT GTVTIVCVAN KYFPDVTVTW EVDGTTQTTG

IENSKTPQNS ADCTYNLSST LTLTSTQYNS HKEYTCKVTQ

GTTSVVQSFN RGDC

The anti-(ox)MIF antibody of the invention is preferably an isolated monoclonal antibody. The anti-MIF antibody can be an IgG, an IgM, an IgE, an IgA, or an IgD molecule. In other embodiments, the anti-MIF antibody is an IgG1, IgG2, IgG3 or IgG4 subclass. In other embodiments, the antibody is either subclass IgG1 or IgG4. In other embodiments, the antibody is subclass IgG4. In some embodiments, the IgG4 antibody has a single mutation changing the serine (serine228, according to the Kabat numbering scheme) to proline. Accordingly, the CPSC sub-sequence in the Fc region of IgG4 becomes CPPC, which is a sub-sequence in IgG1 (Angal et al. Mol Immunol. 1993, 30, 105-108).

Additionally, the production of anti-(ox)MIF antibodies ("oxMIF binders") may include any method known in the art for the purification of an antibody, e.g. via anion exchange chromatography or affinity chromatography. In one embodiment the anti-(ox)MIF antibody can be purified from cell culture supernatants by size exclusion chromatography.

The terms "center region" and "C-terminal region" of MIF refer to the region of human MIF comprising amino acids 35-68 and aa 86-115, respectively, preferably aa 50-68 and aa 86 to 102 of human MIF, respectively. Particularly preferred antibodies (as "oxMIF binders") of the present invention bind to either region aa 50-68 or region aa 86-102 of human MIF. This is also reflected by the binding of the preferred antibodies RAB0, RAB4, RAB2 and RAB9 as well as RAM4, RAM9 and RAM0 which bind as follows:
RAB4 and RAM4: aa 86-102
RAB9 and RAM9: aa 50-68
RAB0 and RAM0: aa 86-102
RAB2: aa 86-102

The term "epitope" includes any protein determinant capable of specific binding to an immunoglobulin or an antibody fragment. Epitopic determinants usually consist of chemically active surface groupings of molecules such as exposed amino acids, amino sugars, or other carbohydrate side chains and usually have specific three-dimensional structural characteristics, as well as specific charge characteristics.

The term "vector" refers to a nucleic acid molecule capable of transporting another nucleic acid to which it has been linked. In some embodiments, the vector is a plasmid, i.e., a circular double stranded DNA loop into which additional DNA segments may be ligated.

The term "host cell" refers to a cell line, which is capable to produce a recombinant protein after introducing an expression vector. The term "recombinant cell line", refers to a cell line into which a recombinant expression vector has been introduced. It should be understood that "recombinant cell line" means not only the particular subject cell line but also the progeny of such a cell line. Because certain modifications may occur in succeeding generations due to either mutation or environmental influences, such progeny may not, in fact, be identical to the parent cell, but are still included within the scope of the term "recombinant cell line" as used herein.

The host cell type according to the present invention is e.g. a COS cell, a CHO cell or e.g. an HEK293 cell, or any other host cell known to a person skilled in the art, thus also for example including bacterial cells, like e.g. E.coli cells. In one embodiment, the anti-MIF antibody is expressed in a DHFR-deficient CHO cell line, e.g., DXB11, and with the addition of G418 as a selection marker. When recombinant expression vectors encoding antibody genes are introduced into CHO host cells, the antibodies are produced by culturing the host cells for a period of time sufficient to allow for expression of the antibody in the host cells or secretion of the antibody into the culture medium in which the host cells are grown.

Anti-(ox)MIF antibodies ("oxMIF binders") can be recovered from the culture medium using standard protein purification methods.

Very surprisingly, the present inventors could show that it was possible and of particular importance to avoid the state of the art-formaldehyde fixation step before binding. If this fixation was carried out using an (inorganic or organic) solvent, even if using the very well known and usually useful fixation agents formaldehyde or acetone, (which are the most commonly used fixation reagents in the field for tissue sections), the MIF in a sample would tend to change its conformation and false positive results could ensue. This could, though this is a theory only, be the result of this fixation agent/solvent inducing structural rearrangements within the MIF protein to result in structures that resemble oxMIF epitopes.

The inventors could show surprisingly that good and reliable results were obtainable if no fixation step was used before the binding step with the primary anti-oxMIF antibody. This is contrary to the expectations of a person skilled in the art who would assume that a fixation step is necessary to provide suitable results, as widely confirmed by practically all usually used methods in that field.

Furthermore, in a particularly preferred embodiment, the secondary detection antibody is an idiotypic monoclonal antibody, preferably an idiotypic rabbit monoclonal antibody. These antibodies have been shown to be particularly advantageous, as they allow the direct detection of an oxMIF binder antibody, e.g. RAM9, without the necessity to label the oxMIF binder. Labelling can sometimes be disadvantageous as it might lead to e.g. a loss of activity. The present secondary antibody (idiotypic) also allow signal amplification and lowering of background noise for the detection method.

The present invention is particularly advantageous, as the inventors were successful in identifying idiotypic monoclonal antibodies directed against the above oxMIF binding antibodies which could reliably and specifically detect these oxMIF binding antibodies which are bound to oxMIF. Thus, the invention—in one embodiment—is directed to antibodies which are idiotypic for the herein described primary antibodies. They also bind specifically to these primary antibodies. Preferably, they bind specifically to these primary antibodies, when the primary antibodies are also bound to oxMIF. In a preferred embodiment, the idiotypic are monoclonal antibodies. In a more preferred embodiment, the idiotypic antibodies are monoclonal rabbit idiotypic antibodies.

The most preferred secondary antibodies are those designated 54-5 and 68-1, both described in more detail above and below. The 54-5 and 68-1 antibodies are anti-RAM9 antibodies.

In a preferred embodiment, the invention provides a method for the provision of such secondary antibodies, wherein an immunization protocol with a Fab-fragment of an oxMIF antibody is performed, followed by a neutralizing ELISA screening. Antibodies are considered suitable as secondary antibodies if they have an $IC_{50}$ of ≤60 ng/ml in the neutralizing ELISA.

In a very preferred embodiment, the idiotypic antibody of this invention is selected from the group of
idiotypic (rabbit) monoclonal anti-RAM9 antibody,
idiotypic (rabbit) monoclonal anti-RAM0 antibody, and
idiotypic (rabbit) monoclonal anti-RAM4 antibody.
Most preferred, the idiotypic antibody is an
idiotypic (rabbit) monoclonal anti-RAM9 antibody.

With these idiotypic monoclonal antibodies, it was advantageously possible to minimize the background noise of earlier methods and to detect oxMIF reliably also in those tissues of patients which had already been treated with an oxMIF binding antibody, like e.g. RAM9.

The rabbit idiotypic monoclonal antibodies of this invention mimic the binding epitope of oxMIF. They do not itself bind to oxMIF, but bind the primary oxMIF binding antibodies instead and thus improve signal strength. They specifically bind the primary antibodies. It was very surprising that it was possible to provide such specific antibodies with an immunization protocol using a Fab-fragment. "Specific binding" is defined via the $IC_{50}$ value. Antibodies are considered suitable as secondary antibodies and as specifically binding if they have an $IC_{50}$ of ≤60 ng/ml in the neutralizing ELISA. The neutralizing ELISA is described below in more detail as "secondary" ELISA.

The invention also discloses a method to provide such secondary antibodies. In particular, Fab-fragments of anti-oxMIF antibodies are used for immunization. In a preferred embodiment, the Fab-fragment of RAM9 is used for immunization of rabbits. Preferably, immunization is carried out as described in detail in Example 3 hereinafter. Immunization protocols are well known to the person skilled in the art. After immunization, those animals showing highest immune response are selected. A preferred method to monitor the immune response is a differential ELISA, in particular the primary screening ELISA described below. This ELISA is e.g. carried out by using the anti-oxMIF antibody versus a control, see also Example 3. Rabbit lymphocytes, obtained by standard protocols are fused with suitable partner cells and suitable, well-known cloning and sub-cloning steps are performed (see Example 3).

Preferably, a primary screening ELISA is performed. The primary screening uses the anti-MIF antibody and a non-specific human isotype and/or purified total human IgG (as negative controls). Binding of the secondary antibodies is determined. Antibodies are considered as suitable in this primary screening if their signal is at least 50-fold higher towards the anti-RAM antibody then that of the negative control.

In a secondary screening, those antibodies considered suitable in the primary screening are further evaluated. (Human) MIF is coated on an ELISA plate. Samples of secondary antibodies are added. Serial dilutions of anti-oxMIF antibodies are then used for calibration. An $IC_{50}$ of ≤60 ng/ml is considered as suitable and advantageous.

In a preferred embodiment of the present invention the sections of the tissue samples should have a thickness of 2 to 15 µm. In a more preferred embodiment these sections have a thickness of 5 to 10 µm. A preferred thickness is 10 µm.

The biopsies itself were prepared according to state of the art technique known to the person skilled in the art, either fresh frozen or e.g. OCT embedded and sections with the thickness as indicated above were prepared. The steps of the following method and the staining procedure are done at ambient temperature preferably, if not indicated otherwise.

In a preferred embodiment, the sections are air-dried for 20 to 45 minutes, preferably around 30 minutes before the actual procedure starts.

In a preferred embodiment of the method of the present IHC assay, the sample, in particular the tissue sample, is not fixated, in particular not fixated with any inorganic or organic fixation agent or solvent, like formaldehyde or acetone. It is however possible in an optional embodiment to dry the sample before the first binding. It is particularly important that the drying step be carried out in a fashion that avoids oxidation of the sample, and in particular the (ox) MIF presumably comprised therein. Air-drying could be shown by the present inventors to fulfill this requirement. The drying step needs to be carried out without drying components, like e.g. alcoholic components, which have oxidative properties.

In particular, the present inventors could show that by using no fixation procedure before the first binding step (which means also no fixation before the optional blocking step), it is possible to avoid the oxidation of the MIF; using other procedures, it is possible that the MIF structure is re-arranged and thus, would lead to false positive results in the subsequent binding of the antibodies to oxMIF. The samples can however be air-dried before the first binding step.

For the specific binding with the binding compounds of the present invention, preferably the above described primary anti-oxMIF antibodies are used. These antibodies do not need to be biotinylated or otherwise labeled. In another embodiment, it is possible to directly detect anti-oxMIF antibodies in the tissue of a patient who has been treated with such an antibody. The detection is then done according to the present method, adapted to this direct detection, as is known to the person skilled in the art. In a non-limiting example, it would be possible to start with airdrying, continue with fixation (e.g. formaldehyde), permeabilization, endogenous peroxidase blocking, blocking with blocking buffer and then proceeding with the addition of idiotypic anti-RAM9 antibodies. Of course, in this embodiment, it is not necessary to add the primary antibody to carry out this particular assay. It is referred to example 4 which is a working embodiment of this method.

The specific binding of the preferred embodiments of the present invention, (i.e. the binding between the primary antibody and oxMIF) can be preceded by use of a blocking buffer in a preferred embodiment which blocks unspecific binding. In an advantageous alternative of this embodiment, the blocking buffer comprises Goat Serum, Serum Albumin and Fish Gelatine in Tris buffered saline (TBS), in a more preferred embodiment 20% Normal Goat Serum, 2% Serum Albumin and 0.2% Fish Gelatine in TBS. In an alternative embodiment the blocking buffer comprises 20% Normal Goat Serum, 2% Bovine Serum Albumin and Gelatine in the Dulbeccos Phosphate Buffered Saline (DPBS). The treatment of the sample with the blocking buffer, prior the specific binding step with the primary anti oxMIF antibodies, is preferably carried out for 15 to 45 minutes, very preferably for 30 minutes. It has been shown that if the blocking buffer treatment is carried out for less than 15 minutes the signal/noise ratio will deteriorate, i.e. the background signal relative to the specific signal becomes too high.

Furthermore, in a preferred embodiment the concentration range for the primary anti-oxMIF antibodies is between 0.3 and 20 µg/ml. Particularly advantageous, the concentration range for the anti oxMIF antibody is between 0.5 and 16 µg/ml, Even more preferred, the concentration range for the anti oxMIF antibody is between 1 and 10 µg/ml dilution buffer, more preferred between 1-5 µg/ml. Preferably, the sections are fully covered with the oxMIF antibody solution, for which purpose 500 µl solution are sufficient in most cases.

The primary anti-oxMIF antibody is preferably diluted in a primary dilution buffer. In a preferred embodiment this primary dilution buffer comprises Bovine Serum Albumin and Fish Gelatine in TBS, in a more preferred embodiment 2% Bovine Serum Albumin and 0.2% Fish Gelatine in TBS. The incubation with the oxMIF antibody is preferably carried out for 30 to 90 minutes, more preferred for 50-70 minutes, very preferably for approximately 60 minutes.

After the binding step, the sections should—in a preferred embodiment—be dipped shortly in fresh TBS (or e.g. DPBS; washing buffer) to wash away excess antibody; in an alternative embodiment, where the blocking buffer and the dilution buffer used the DPBS instead of TBS the dip should be in fresh DPBS. After the dipping, a washing step in fresh washing buffer should be carried out for approximately 5 to 15 minutes, in a more preferred embodiment for 10 minutes.

As an optional, but preferred, step—which should however be carried out only AFTER the first binding step—it is possible to fix the specimen in a suitable fixation solution, e.g. phosphate buffered formaldehyde, for a time period of 10 to 25 minutes, preferably 15 to 20 minutes. This fixation step with formaldehyde is optional, though preferred, and serves to maintain tissue structures. This step has no negative influence on the (ox)MIF structure and does not lead to false positive results.

After this optional step, it is again preferred to dip shortly into TBS (or alternatively DPBS) to wash away excess formaldehyde; the dipping period is as explained above; thereafter it can be incubated for 5-15 min, preferably 10 minutes in fresh TBS (or DPBS, respectively).

Optionally, endogenous peroxidases are then blocked. This can be done by incubating the tissue sections in e.g. $H_2O_2$ in methanol, preferably in 0.3% $H_2O_2$ in methanol for 20-30 minutes. Excess methanol is then preferably removed by washing in TBS for 5-10 minutes. Peroxidase blocking (PB) can also be done with commercial peroxidase blockers e.g. dual endogenous enzyme block from DAKO (see e.g. example 4). If these commercial PB are used a permeabilization step after fixation can be done additionally. A possible working embodiment here would be incubation in TBS+ 0.2% TritonX-100 for 5 minutes.

Alternative methods are known to the person skilled in the art.

The detection step is carried out by adding the idiotypic antibody to the reaction. The idiotypic antibody is supplied in a dilution buffer. The concentration is preferably around 0.5 µg/ml. The dilution buffer is the same as described above for the primary antibody. The preferred incubation time is between 15 and 45 min, more preferred between 20 and 40 min. In an alternative approach, it is also possible to use directly fluorophore labeled or e.g. peroxidase labeled idiotypic antibodies. The person of skill in the art is aware that it would then be possible to proceed directly to washing and developing (peroxidase labeled) or directly to washing and mounting (fluorophore labeled).

After these steps, staining in a suitable staining reagent should be carried out according to the preferred embodiment. This staining can be done with known rabbit IHC detection reagents, like SignalStain® Boost IHC Detection Reagent, Rabbit. Alternatively, other detection methods as known to a person skilled in the art are suitable; e.g. a fluorophore-labelled antibody could be used as a (third) detection tool, e.g. as an Alexa Fluor labelled anti rabbit antibody or by fluorescent labelling of the secondary antibody. Detection with fluorophore labelled entities has been shown to be suitable by the present inventors in the context of this invention (see e.g. Example 2). This is described in more detail, but generally applicable in example 3, as an alternative procedure. A preferred staining reagent is a SignalStain Boost IHC Detection Reagent, Rabbit. The staining period should last at least 20 minutes, preferably at least 30 minutes, in a very preferred embodiment at least 45 minutes. As is known to the person skilled in the art, it is also possible to use a suitable tertiary antibody for detection of the binding between primary and secondary antibody Preferably, the sections are again dipped shortly in TBS (alternatively DPBS, see above) to wash away excess secondary reagent; thereafter in a preferred embodiment a further incubation for 5 to 15 minutes, preferably 10 minutes in fresh TBS or fresh DPBS is carried out.

The resultant slides are in a preferred embodiment developed with a substrate e.g. a substrate suitable for development, as well known to a person skilled in the art, e.g. the ImmPACT DAB substrate for 1 to 10 minutes, preferably 5 minutes.

Thereafter, in a preferred embodiment the sections are then shortly dipped in TBS (or DPBS see above) to wash away excess substrate and are then incubated for 5 to 15 minutes, preferably 10 minutes in fresh TBS or alternatively DPBS.

After the above step, a counterstaining step to stain the nuclei is preferably carried out; all well-known staining agents for immunohistochemistry procedures can be used here. In a preferred embodiment hematoxylin is used.

The staining should be carried out for 0.5 to 3 minutes, preferably 1 to 2 minutes.

The sections are thereafter rinsed with tap water and dipped shortly (preferably in tap water again) to wash away excess staining reagent. Thereafter, in an optional embodiment it is incubated for 1 to 5 minutes, preferably 1 to 2 minutes. The incubation time varies and depends on the emergence of the color change form violet to blue in the case of hematoxylin.

For microscopy, the tissue sections are preferably dried, as is well known to a person skilled in the art, in e.g. 70%, following 90%, and absolute ethanol for e.g. 2 min each and afterwards preferably cleared in e.g. Xylene for e.g. at least 3 min. In an alternative embodiment the drying step is done in 96% to absolute ethanol for 2×20 seconds. For long term storage the sections were mounted using VECTASTAIN Permamount and covered with a cover slip. Drying and mounting steps are part of the general knowledge of a person skilled in the art.

The present invention is further explained by way of the following examples, which shall however by no means limit the scope of this invention which is determined by the claims.

EXAMPLES

Example 1: oxMIE In Situ Detection by Immunohistochemistry (IHC) in Pancreas from an Infiltrating Ductal Carcinoma Patient (FIG. 1)

Cryosections of a biopsy from a 64 year old infiltrating ductal carcinoma patient was obtained commercially. Detection of oxMIF was examined using RAM9 or without RAM9, with anti-idiotypic monoclonal rabbit RAM9 antibody.

Material and Methods

The slides were prepared according to state of the art techniques known to experts, either fresh frozen or OCT embedded, sectioned at 10 µm and stored at <=−80° C. after sectioning. All following steps were done at ambient temperature. The cryo-sections were air dried for 30 min and unspecific binding was blocked with blocking buffer (BB: 20% Normal Goat Serum/2% Bovine Serum Albumin/0.2% Fish Gelatine in TBS) for 15 min. The sections were then incubated without primary antibody or with anti-oxMIF antibody RAM9 in primary antibody dilution buffer (PADB: 2% Bovine Serum Albumin/0.2% Fish Gelatine in TBS) at a concentration of 2 µg/ml for 60 min. After washing in TBS, the specimen was fixed in 4% PBS buffered formaldehyde for 20 min. Excess formaldehyde was removed by washing in TBS for 5-10 min, Endogenous peroxidases were blocked by incubating the tissue sections in 0.3% $H_2O_2$ in methanol for 20 min. Excess methanol/$H_2O_2$ was removed by washing in TBS for 5-10 min. Detection of was done by incubating the tissue sections with anti-idiotypic rabbit monoclonal antibodies (68-1) diluted in PADS at 1 µg/ml for 30 min. Excess detection antibody was removed by washing in TBS for 5-10 min. The staining was done using SignalStain® Boost IHC Detection Reagent—Rabbit for 30 min. Then the sections were extensively washed again 10 min in TBS. By using ImmPACT DAB Substrate for 5 minutes the staining was visualized as a brown color. The slides were washed in TBS and the nuclei were counterstained with Haematoxylin for 1-2 min. By washing the slides in tab water the color of the counter stain changes from violet to blue. For microscopy, the tissue sections were dried in 96% following absolute ethanol for 2×20 sec each and afterwards cleared in Xylene for 2 min. For long term storage the sections were mounted using VECTASTAIN Permamount and covered with a cover slip.

Results oxMIF was detected in the pancreas from a patient suffering infiltrating ductal carcinoma of the pancreas, with a main staining in the PanIN ductal structures (dark grey staining; i.e. dark grey in FIG. 1A), as compared to normal pancreatic tissue where no staining was observed (data not shown), The dark structures (dot-like in the attached FIG. 1A) observed in the sections are the nuclei from the cells (hematoxylin staining). To be noted, no staining was detected in the cryo-sections from normal or cancerous pancreas tissue, when staining was performed using the same conditions without the above mentioned primary detection antibody (FIG. 1B).

By carrying out additional research the inventors could determine that in a preferred embodiment sections with a thickness of 2 to 16 µm, or 5-10 µm were particularly advantageous. Furthermore, a concentration range for the primary anti-oxMIF antibody of 0.5 to 16 µg/ml, preferably 0.5-5 µg/ml, was shown to be particularly advantageous.

Conclusion

In diseased organs such as pancreas from patients suffering infiltrating ductal carcinoma of the pancreas, oxMIF can be detected in situ by means of the present IHC techniques, whereas it is absent from a healthy pancreatic tissue.

Example 2 (FIG. 2):

in situ detection of oxMIF by immunofluorescence in a tissue biopsy of a human lung was carried out. The samples were from a normal lung (FIG. 2A) of a 66 year old female donor and from a squamous cell carcinoma from a 61 year old female patient (FIG. 2B).

Procedure:

The slides were prepared according to state of the art techniques known to experts, either fresh frozen or OCT embedded, sectioned at 10 µm and stored at <=−80° C. after sectioning. All following steps were carried out at ambient temperature. The cryo-sections were air dried for 30 min and unspecific binding was blocked with blocking buffer (BB: 20% Normal Goat Serum/2% Bovine Serum Albumin 10.2% Fish Gelatine in TBS) for 20 min. The sections were then incubated with anti oxMIF antibody RAM9 in primary antibody dilution buffer (PADB: 2% Bovine Serum Albumin/0.2% Fish Gelatine in TBS) at a concentration of 5 µg/ml for 60 min. After washing in TBS, the specimen was fixed in 4% PBS buffered formaldehyde for 20 min. Excess formaldehyde was removed by washing in TBS for 5-10 min. The tissue sections were permeabilized by incubating in methanol for 5 min. (Alternatively, 5-10 min PADB+ 0.25% TritonX-100 is also feasible). Excess methanol was removed by washing in TBS for 5-10 min (tissue sections were not dried). Detection of RAM9 was done by incubating the tissue sections with anti-idiotypic rabbit monoclonal anti-RAM9 antibodies diluted in PADB at 1 µg/ml for 30 min. Excess detection antibody was removed by washing in TBS for 5-10 min. The staining was done using an Alexa Fluor®555 labeled anti-rabbit antibody diluted in PADB at 2 µg/ml for 30 min. Then the sections were extensively washed 10 min in PBST (PBS+0.1% Tween20). For microscopy, the tissue sections were mounted in ProLong® Gold Antifade Reagent with DAPI (nuclear counterstain).

Results

Clear staining of oxMIF in the carcinoma tissue could be observed with the present inventive method. No staining was seen in the normal lung.

Conclusion

In diseased organs such as lung from patients suffering squamous cell carcinoma of the lung, oxMIF can be detected in situ by means of the present IF techniques whereas it is absent from a healthy lung tissue.

Example 3

Generation of Monoclonal Rabbit RAM9 Anti-idiotypic Antibodies

Material and Methods

Immunization Procedure for Monoclonal Rabbit Anti oxMIF Antibodies

To generate specific monoclonal rabbit idiotypic antibodies, rabbits were immunized with Fab fragments of RAM9 generated by papain digest and subsequent purification on a Poros S Ion exchange column. Purity was confirmed after SDS-PAGE by Coomassie staining.

The immunization was done using a standard immunization of five injections.

For the initial immunization: 0.4 mg recombinant RAM9-Fab was mixed with an aliquot of CFA (Complete Freund's Adjuvant). The animals received 200 µl (4×50 µl) of the mixture subcutaneously. The boost immunizations were performed in 3 week-intervals with 0.2 mg dose per animal as described above using IFA (Incomplete Freund's Adjuvant). Sera were taken prior to the first, one in between and after the final immunization boost and tested by primary screening ELISA. After the last boost, the rabbits were humanely euthanized by intravenous injection of barbiturate.

Cell Fusion

Splenectomies were performed on the rabbits showing the highest immune response monitored by primary screening ELISA (RAM9 versus human control antibody pre-coated, detected by goat anti rabbit IgG/HRP). The spleens were submerged in fresh Petri dish filled with RPMI 1640 with 1% penicillin/streptomycin/fungizone, washed several times and crushed into pieces using a sterile plunger of a 3 ml syringe. Lymphocytes were separated from debris by putting the crushed spleen through two 100 µm-cell strainers. After several washes, $2 \times 10^8$ rabbit lymphocytes were fused with $1 \times 10^8$ fusion partner cells and plated on twenty 96-well plates per fusion.

Generation of Multiclones and Subcloning

Multiclone supernatants were tested against the immunogen (RAM9) by primary screening ELISA. Selected positive multiclones were sub-cloned using the limited cell dilution method. Supernatants from the subclones were tested as described above. The best clones were used for the production of rabbit anti RAM9 antibodies in a medium scale process.

Production of Monoclonal Rabbit Anti-RAM9 Antibodies.

Starting from a frozen cell vial, each hybridoma clone was seeded in 15 ml of a cell culture medium supplemented with 2-mercaptoethanol, penicillin/streptomycin and 5% Ultra Low IgG FBS in a 125 ml shake flask and incubated at 37° C. in a 5% $CO_2$ atmosphere by shaking at 120 rpm. The culture was expended to higher volumes and supernatants were taken regularly.

At the end of fermentation, the cell culture supernatant was centrifuged to remove cells and debris. After filtration through a 0.2 µm membrane the supernatants were stored at ≤−20° C. or were immediately applied to antibody purification.

Purification of Monoclonal Rabbit Anti-RAM9 Antibodies

The cell culture supernatant of rabbit hybridomas producing the antibody was applied to a HiTrap MabSelect Sure column (GE Healthcare). Impurities were removed by washing with 10 column volumes of a 20 mM Na$_2$HPO$_4$ buffer at pH 7.2. Elution of the monoclonal anti-RAM9 antibodies was performed at low pH conditions using a 100 mM glycin buffer at pH 2.8. The one step purified monoclonal antibodies were then neutralized by dilution in PBS (pH 7.2), concentrated and stored at −20° C. for further experiments.

Cloning and Production of Selected Monoclonal Rabbit Anti-RAM9 Antibodies in HEK293 Cells mRNA from hybridoma cells was isolated using the commercially available TuboCapture Kit (Qiagen: Catalog 72232) following the manufacturer's suggestions and then reverse transcribed into cDNA using oligo-dT primer. The variable region of the heavy chain (VH) was PCR amplified. The entire light chain (LC) was PCR amplified. The VH region of PCR fragments was digested using the restriction enzyme HindIII and KpnI. The LC PCR fragments were digested using HindIII and NotI. All digested product was purified using Qiagen PCR cleaning up kit (catalog #28016). After purification, the VH or LC fragment was ligated into a corresponding heavy or light chain expression vector and transformed into competent cells DH5a (MC Lab, catalog #DA-100). The transformed colonies were picked and inserts were confirmed (by expected size: approximately 440 bp for VH and 740 bp for LC) using the corresponding restriction enzymes. Plasmids with inserts of the expected size were sequenced (SEQ ID NO 15-18). The light chain and heavy chain were co-transfected into HEK293 cells in 6-well plates. The supernatants were collected four days post transfection and tested against corresponding antigen in a primary screening ELISA. Furthermore the concentration of rabbit IgG was determined. The best producing specific clone was chosen for large scale production. The cell culture supernatants were then purified as described above.

Furthermore, the entire light chain or heavy chain fragment was excised from the corresponding expression vector with HindIII and NotI and subsequently purified using Qiagen PCR cleaning up kit (catalog #28016). The cDNA inserts were cloned into pcDNA3.1 plasmids.

Primary Screening ELISA

RAM9 (target) and a non-specific human isotype and/or purified human total IgG (negative controls) were immobilized onto microplates at 1 µg/ml in PBS using 100 µl/well. Microplates were blocked with 200 µl 20% HSA (human serum albumin)/TBST (TBS with 0.1% Tween20). Washing steps are included between all incubations. Cell culture supernatants of the rabbit hybridoma cell lines were applied to these microplates at selected dilutions in 30% HSA/TBST. The binding of the anti-RAM9 antibodies was determined using a goat anti-rabbit IgG (H+L)-HRP detection antibody. The signal was developed using either TMB or another chromomeric peroxidase substrate. Specific antibodies showed at least 50 fold higher signal towards RAM9 compared to negative controls (see FIG. 3).

Secondary Screening ELISA

Microplates were coated with human MIF (10 µg/ml PBS, 100 µl/well) and blocked with 250 µl 1.5% fish gelatin in PBS. Washing steps (4×250 µl of PBS per well) were included between the incubations. The samples were serially pre-diluted (in 1% fish gelatin/PBS) to 2× final dilution and mixed with an equivalent volume of biotinylated RAM9 (30 ng/ml) (equivalent to a 1:2 dilution, final concentration of RAM9 is therefore 15 ng/ml). These mixtures were allowed to form complexes for 30 min. Serial dilutions of biotinylated RAM9 (25-0.2 ng/ml) in 1% fish gelatin/PBS were used for calibration and 15 ng/ml biotinylated RAM9 was used in a negative control (corresponds to the final concentration of biotinylated RAM9 in the same preparation). The samples (100 µl/well) were applied to the microplate for 2 hours. Biotinylated RAM9 captured on the plate was detected using HRP coupled Streptavidin and TMB as chromogenic substrate. The absorbance of each well was related to the absorbance of the standard curve by linear regression and is expressed in ng/ml. The concentration calculated for biotinylated RAM9 in the sample is related to the calculated concentration of biotinylated RAM9 in the negative control (% recovery=(100%/measured concentration of biotinylated RAM9 in the negative control)×measured concentration of RAM9 in the sample). Half maximal binding inhibition (IC$_{50}$) by anti-RAM9 antibodies is calculated by blotting log concentration of rabbit anti-RAM9 against % recovery and non-linear 4-parameter curve fit with variable slope FIG. 4a.

After a final purification step, two particularly promising antibodies (designated 68-1 and 54-5) were again tested in the above described secondary screening and reached an IC$_{50}$ of as good as 29.65 or 68-1 and 5.958 for 54-5, respectively, see FIG. 4b.

Both antibodies are very suitable as secondary detection antibodies. See e.g. the in situ detection of oxMIF in infiltrating ductal carcinoma in FIGS. 1 and 5.

Example 4

Detection of RAM9 in Tissue

Lymph nodes from a chronic lymphocytic leukemia mouse model, where one group was treated with RAM9 and one group with antibody vehicle, were fresh frozen and OCT embedded. The tissue blocks were cryo-sectioned at 10 µm and stored at ≤−80° C. after sectioning. All following steps were done at ambient temperature. The cryo-sections were air dried for 30 minutes following fixation in 4% PBS buffered formaldehyde for 15-20 minutes. Simultaneously, tissue sections were permeabilized and excess formaldehyde was removed by washing in TBS+0.2% TritonX-100 for 5-10 minutes. Endogenous peroxidases were blocked by incubating the tissue sections with dual endogenous enzyme block (Dako) for 10 minutes. Excess dual endogenous enzyme block was removed by washing in TBS for 5-10 minutes. Unspecific binding was blocked with blocking buffer (BB: 20% Normal Goat Serum/2% Bovine Serum Albumin/0.2% Fish Gelatine in TBS) for 15-20 minutes. Detection of RAM9 was achieved by incubating the tissue sections with monoclonal rabbit anti-RAM9 antibodies (68-1) diluted in PADB 0.5 µg/ml for 30 min. Excess detection antibody was removed by washing in TBS for 5-10 minutes. The staining was done using a highly cross adsorbed goat anti-rabbit HRP conjugate (Thermo Scientific) diluted in PDAB at 1.6 µg/ml for 30 min minutes. Then the sections were extensively washed again 10 min in TBS. By using DAB Substrate (Dako) for 5-10 minutes the staining was visualized. The slides were washed in TBS and the nuclei were counterstained with Haematoxylin for 10 seconds to 1 minute. By washing the slides in tap water the color of the counter stain changes from violet to blue. For microscopy, the tissue sections were dried in 96 following absolute ethanol for 2×20 seconds each and afterwards cleared in Xylene for approximately 3 minutes. For long term storage, the sections were mounted using VECTASTAIN Permamount and covered with a cover slip.

Results:

In diseased organs such as lymph nodes from mice suffering chronic lymphocytic leukemia, RAM9 bound to oxMIF (black arrows) can be detected in situ by means of the present IHC techniques (FIG. 6A). No background staining was observed in lymph nodes from vehicle treated control mice (FIG. 6B).

Example 5

The purpose of this example was the semi-quantitative determination of the amount of RAM9 that is able to penetrate and accumulate in malignant tissue after therapeutic intravenous application and to correlate it to semi-quantitatively determine the amount of the target (=oxMIF) in the same tissue area on two consecutive slides of the tumor biopsy. 100% target saturation is achieved, if the semi-quantitatively determined amount of RAM9 and oxMIF (=target) equal each other.

Animal Model:

Lymph nodes from a chronic lymphocytic leukemia mouse model, where one group was treated with RAM9 and one group with antibody vehicle, were resected and snap frozen. The frozen lymph nodes were embedded in OCT, to prepare a tissue micro array (all lymph nodes from one group in one tissue block). The tissue blocks were cryosectioned at 10 µm and stored at ≤−80° C. after sectioning.

Immunohistochemistry:

Staining for RAM9 was carried out as described in Example 4 supra.
- this method detects RAM9 that was applied in vivo, but does not discriminate between RAM9 that is bound to oxMIF and free RAM9 that accumulates in the tissue Staining for oxMIF (target):
- this method detects RAM9 bound to oxMIF and oxMIF that was not already bound by RAM9 (free oxMIF) that was applied in vivo. By applying exogenous RAM9 to the unfixed tissue, oxMIF that was not already bound by in vivo applied RAM9 is saturated. A rinse after exogenous RAM9 applications and before tissue fixation avoids detection of unbound RAM9, whereupon only oxMIF is detected by this immunohistochemical method.

All following steps were done at ambient temperature. The cryo-sections were air dried for 30 minutes and unspecific binding was blocked with blocking buffer (BB: 20% Normal Goat Serum/2% Bovine Serum Albumin/0.2% Fish Gelatine in TBS) for 15-20 minutes. oxMIF was detected by incubation of the section with RAM9 diluted in PADB (2% Bovine Serum Albumin/0.2% Fish Gelatine in TBS) at 1 µg/ml for 30 min. Excess RAM9 was removed by rinse in TBS for 5-10 minutes. Following fixation in 4% PBS buffered formaldehyde for 15-20 minutes the tissue sections were permeabilized and excess formaldehyde was removed by washing in TBS+0.2% TritonX-100 for 5-10 minutes. Endogenous peroxidases were blocked by incubating the tissue sections with dual endogenous enzyme block (Dako) for 10 minutes. Excess dual endogenous enzyme block was removed by washing in TBS for 5-10 minutes. Detection of RAM9 was done by incubating the tissue sections with monoclonal rabbit anti-RAM9 antibodies diluted in PADB at 0.5 µg/ml for 30 min. Excess detection antibody was removed by washing in TBS for 5-10 minutes. The staining was done using a highly cross adsorbed goat anti-rabbit HRP conjugate (Thermo Scientific) diluted in PDAB at 1.6 µg/ml for 30 min minutes. Then the sections were extensively washed again 10 min in TBS. By using DAB Substrate (Dako) for 5-10 minutes the staining was visualized. The slides were washed in TBS and the nuclei were counterstained with Haematoxylin for 10 seconds to 1 minute. By washing the slides in tab water the color of the counter stain changed from violet to blue. For microscopy, the tissue sections were dried in 96% following absolute ethanol for 2×20 seconds each and afterwards cleared in Xylene for approximately 3 minutes. For long term storage, the sections were mounted using VECTASTAIN Permamount and covered with a cover slip. The full slides were scanned by an Olympus slide scanning microscope (VS120) at 20× magnification.

Evaluation:

Digital full slide images were analyzed using Definiens Tissue Studio™ V3.6. The tissue area mark-up was either done manually or automated by the software. Areas of necrosis or tissue folds were excluded from further analysis. Once the tissue area was marked up the software was able to distinguish between the brown immunostain (oxMIF or RAM9) and the blue counterstain (Haematoxylin) and to calculate the area of immunostaining in the whole tissue area. Dividing the calculated stained area (%) of RAM9 staining by the calculated stained area (%) of oxMIF (=target) staining results in the ratio of target saturation.

Figure 8:
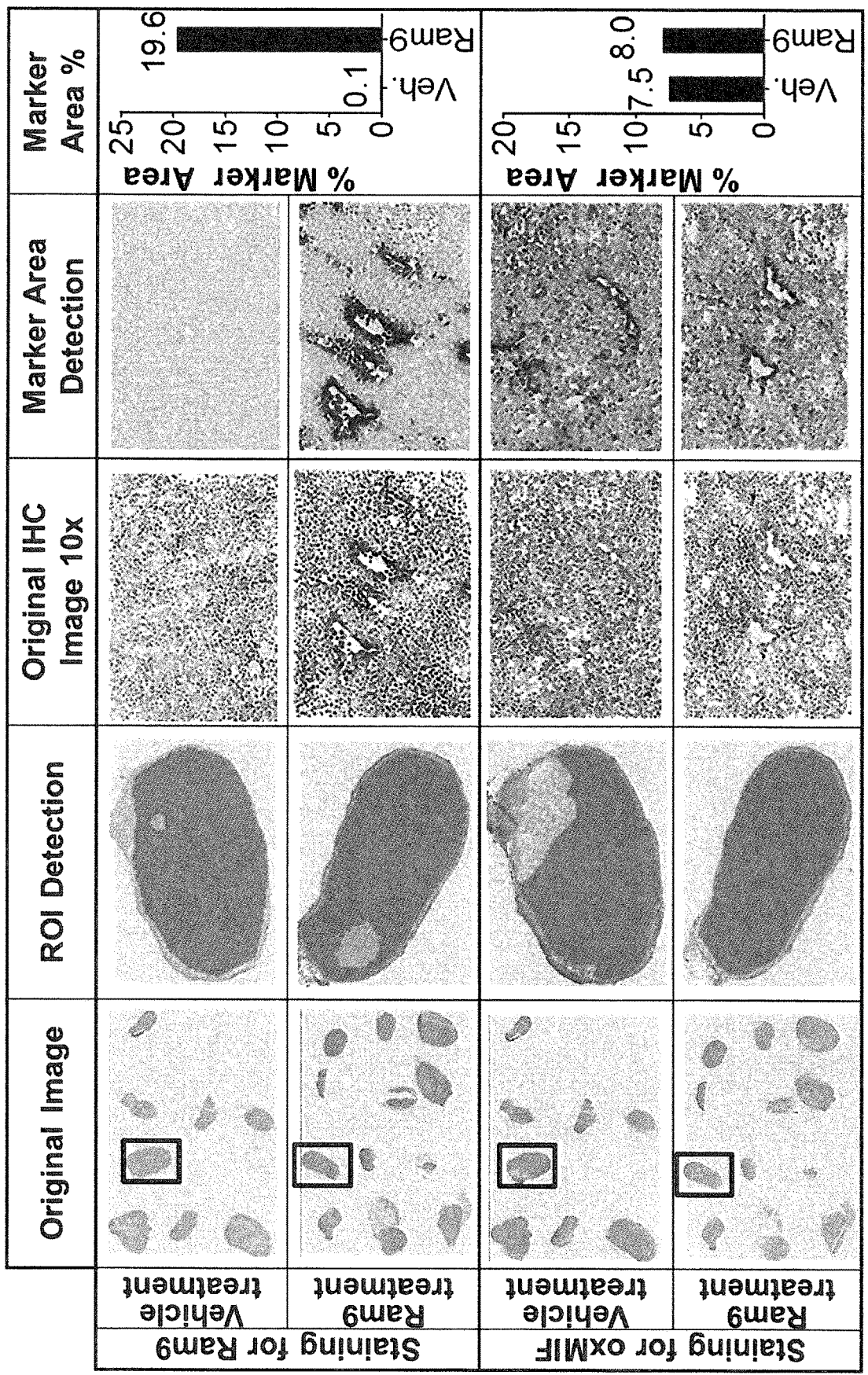

The results are shown in FIGS. 8-9. The method is very suitable to achieve a determination of target saturation and thus enable both suitability of the treatment as well as provide predictions for treatment success.

Example 6

The methods described in the example 5 above were applied to biopsies obtained from a patient with advanced metastatic colorectal cancer. The patient was treated with 10 mg/kg RAM9 every week for 7 months. Biopsies were taken prior to the first RAM9 application, and after 1 month, 2 months and 6 months treatment with RAM9. The biopsies were snap frozen in $N_2$, embedded in OCT and sectioned at 10 µm. The cryosections were subjected to immunohistochemical analysis for oxMIF and RAM9, Evaluation of target saturation was done as described in Example 5. In addition to the previous example a pathologist marked up tumor cells during digital image analysis in the biopsies. Therefore, it was possible to calculate target saturation in tumor cells, stroma (total tissue area−tumor cell area) and in the total tissue area.

Result:

Treatment of the patient with 10 mg/kg RAM9 once a week resulted in an accumulation of RAM9 in tumor cells and in stromal tissue in the course of treatment. Data are represented as mean of 2-5 biopsies from one patient per time point with error bars indicating the range (see FIG. 10).

The invention claimed is:

1. An immunohistochemistry (IHC) assay method for in vitro detection of oxMIF (oxidized macrophage migration inhibitory factor), wherein oxMIF is MIF which is differentially binding to antibody RAB4, RAB9 and RAB0, in a tissue sample of a subject, the IHC assay method comprising the determination of the binding of a primary anti-oxMIF antibody to oxMIF in said sample in vitro, wherein said primary anti-oxMIF antibody is RAIVI9, wherein the following steps are carried out:

a) Optional Blocking step with blocking buffer;
b) Binding step with said primary anti-oxMIF antibody without a previous fixation step, in either formaldehyde or acetone; wherein a washing step is carried out after binding step b) to wash away excess antibody;
c) Fixation step, wherein said fixation is carried out in formaldehyde for 10-25 minutes;
d) Incubation with secondary antibody, wherein the secondary antibody is an idiotypic rabbit monoclonal antibody directed against an anti-oxMIF antibody, wherein the secondary antibody is characterized by a heavy chain comprising SEQ ID NO: 15 and a light chain comprising SEQ ID NO: 16, or by a heavy chain comprising SEQ ID NO: 17 and a light chain comprising SEQ ID NO: 18; and
   e) Detection of binding between the primary anti-oxMIF antibody and the secondary antibody.

2. The IHC assay of claim 1, wherein the samples is air dried for about 30 min.

3. The IHC assay of claim, wherein the primary antibody is not labelled and is comprised in a primary dilution buffer and wherein the primary antibody is incubated with the sample for 45 to 90 minutes.

4. The IHC assay of claim, wherein optionally further washing steps are carried out after all further steps.

5. The IHC assay of claim 1, wherein the detection step e) comprises or consists of a staining step and wherein a further (counter)staining step is carried out after the detection step, which can include the use of a tertiary antibody.

6. The IHC assay of claim 1, wherein the (counter) staining step is carried out with hematoxylin, after step e).

7. The IHC assay of claim 1, wherein the binding between the primary and secondary antibody is detected by fluorescence, or a directly fluorescence labelled secondary antibody by use of a fluorophore labelled tertiary antibody directed against the secondary antibody.

8. The IHC assay of claim 1, wherein said secondary antibody is a secondary monoclonal anti-RAM9 antibody.

9. The IHC assay of claim 1, wherein the sample is selected from the group consisting of a tissue biopsy, a frozen tissue biopsy, an OCT (Optimal Cutting Temperature) embedded section, and a core needle biopsy.

10. The IHC assay of claim 1, wherein said secondary antibody is characterized by a heavy chain which has been deposited at the DSMZ with deposit No. DSM 28180 (SEQ ID No. 17) and by a light chain, which has been deposited at the DSMZ with deposit No. DSM 28181 (SEQ ID No. 18); or which is characterized by a heavy chain which has been deposited at the DSMZ with deposit No. DSM 28182 (SEQ ID No. 15) and a light chain which has been deposited at the DSMZ with a deposit no. DSM 28183 (SEQ ID No. 16).

11. An IHC assay kit, adapted to carry out the method according to claim 1; comprising:
   1) an idiotypic antibody which is characterized by a heavy chain which has been deposited at the DSMZ with deposit No. DSM 28180 (SEQ ID No. 17) and by a light chain, which has been deposited at the DSMZ with deposit No. DSM 28181 (SEQ ID No. 18); or which is characterized by a heavy chain which has been deposited at the DSMZ with deposit No. DSM 28182 (SEQ ID No. 15) and a light chain which has been deposited at the DSMZ with a deposit no. DSM 28183 (SEQ ID No. 16), and
   2) an anti-oxMIF antibody.

12. The IHC assay of claim 1, wherein said primary anti-oxMIF antibody is RAM9 and said secondary antibody is characterized by a heavy chain which has been deposited at the DSMZ with deposit No. DSM 28180 (SEQ ID No. 17) and by a light chain, which has been deposited at the DSMZ with deposit No. DSM 28181 (SEQ ID No. 18); or which is characterized by a heavy chain which has been deposited at the DSMZ with deposit No. DSM 28182 (SEQ ID No. 15) and a light chain which has been deposited at the DSMZ with a deposit no. DSM 28183 (SEQ ID No. 16).

13. The IHC assay of claim 1, wherein said secondary antibody is characterized by a heavy chain which has been deposited at the DSMZ with deposit No. DSM 28180 (SEQ ID No. 17) and by a light chain, which has been deposited at the DSMZ with deposit No. DSM 28181 (SEQ ID No. 18).

14. The IHC assay of claim 1, wherein said secondary antibody is characterized by a heavy chain which has been deposited at the DSMZ with deposit No. DSM 28182 (SEQ ID No. 15) and a light chain which has been deposited at the DSMZ with a deposit no. DSM 28183 (SEQ ID No. 16).

* * * * *

SEQUENCE LISTING

<160> NUMBER OF SEQ ID NOS: 18

<210> SEQ ID NO 1
<211> LENGTH: 214
<212> TYPE: PRT
<213> ORGANISM: Artificial Sequence
<220> FEATURE:
<223> OTHER INFORMATION: Light chain of RAB9

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Arg Ile Met Thr Tyr
            20                  25                  30

Leu Asn Trp Tyr Gln Gln Lys Pro Gly Lys Ala Pro Lys Leu Leu Ile
        35                  40                  45

Phe Val Ala Ser His Ser Gln Ser Gly Val Pro Ser Arg Phe Arg Gly
    50                  55                  60

Ser Gly Ser Glu Thr Asp Phe Thr Leu Thr Ile Ser Gly Leu Gln Pro
65                  70                  75                  80

Glu Asp Ser Ala Thr Tyr Tyr Cys Gln Gln Ser Phe Trp Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 214
<212> TYPE: PRT
<213> ORGANISM: Artificial Sequence
<220> FEATURE:
<223> OTHER INFORMATION: Light chain of RAB4

<400> SEQUENCE: 2

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Ala Ser Gly Thr Asp Phe Thr Leu Thr Ile Ser Arg Leu Gln
65                  70                  75                  80

```
Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 214
<212> TYPE: PRT
<213> ORGANISM: Artificial Sequence
<220> FEATURE:
<223> OTHER INFORMATION: Light chain of RAB0

<400> SEQUENCE: 3

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
                20                  25                  30

Ser Leu Ala Trp Tyr Gln Gln Lys Pro Gly Gln Ala Pro Arg Leu Leu
            35                  40                  45

Ile Tyr Gly Thr Ser Ser Arg Ala Thr Gly Ile Pro Asp Arg Phe Ser
    50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 4
<211> LENGTH: 214
<212> TYPE: PRT
<213> ORGANISM: Artificial Sequence
<220> FEATURE:
<223> OTHER INFORMATION: Light chain of RAB2

<400> SEQUENCE: 4

Asp Ile Gln Met Thr Gln Ser Pro Val Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Thr Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 445
<212> TYPE: PRT
<213> ORGANISM: Artificial Sequence
<220> FEATURE:
<223> OTHER INFORMATION: Heavy chain of RAB9

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ser Met Asn Trp Val Arg Gln Ala Pro Gly Lys Gly Leu Glu Trp Val
        35                  40                  45

Ser Ser Ile Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Gly Ser Gln Trp Leu Tyr Gly Met Asp Val Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
    275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 6
<211> LENGTH: 454
<212> TYPE: PRT
<213> ORGANISM: Artificial Sequence
<220> FEATURE:
<223> OTHER INFORMATION: Heavy chain of RAB4

<400> SEQUENCE: 6

Glu Val Gln Leu Leu Glu Ser Gly Gly Gly Leu Val Gln Pro Gly Gly
1               5                   10                  15

-continued

```
Ser Leu Arg Leu Ser Cys Ala Ala Ser Gly Phe Thr Phe Ser Ile Tyr
            20                  25                  30

Ala Met Asp Trp Val Arg Gln Ala Pro Gly Lys Gly Leu Glu Trp Val
            35                  40                  45

Ser Gly Ile Val Pro Ser Gly Gly Phe Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Cys Ser Arg Ser
 130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
            195                 200                 205

Thr Cys Asn Val Asp His Lys Pro Ser Asn Thr Lys Val Asp Lys Arg
 210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
            275                 280                 285

Val Glu Val His Asn Ala Lys Thr Lys Pro Arg Glu Glu Gln Phe Asn
 290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
            355                 360                 365

Gln Val Ser Leu Thr Cys Leu Val Lys Gly Phe Tyr Pro Ser Asp Ile
 370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430
```

```
Ser Val Met His Glu Ala Leu His Asn His Tyr Thr Gln Lys Ser Leu
        435                 440                 445

Ser Leu Ser Leu Gly Lys
    450
```

<210> SEQ ID NO 7
<211> LENGTH: 454
<212> TYPE: PRT
<213> ORGANISM: Artificial Sequence
<220> FEATURE:
<223> OTHER INFORMATION: Heavy chain of RAB0

<400> SEQUENCE: 7

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ala Met Asp Trp Val Arg Gln Ala Pro Gly Lys Gly Leu Glu Trp Val
        35                  40                  45

Ser Gly Ile Tyr Pro Ser Gly Arg Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335
```

```
Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
                355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
                435                 440                 445

Ser Leu Ser Leu Gly Lys
            450

<210> SEQ ID NO 8
<211> LENGTH: 454
<212> TYPE: PRT
<213> ORGANISM: Artificial Sequence
<220> FEATURE:
<223> OTHER INFORMATION: Heavy chain of RAB2

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Asp Trp Val Arg Gln Ala Pro Gly Lys Gly Leu Glu Trp Val
        35                  40                  45

Ser Gly Ile Val Pro Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240
```

-continued

```
Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
    450

<210> SEQ ID NO 9
<211> LENGTH: 457
<212> TYPE: PRT
<213> ORGANISM: Artificial Sequence
<220> FEATURE:
<223> OTHER INFORMATION: RAM0hc

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ala Met Asp Trp Val Arg Gln Ala Pro Gly Lys Gly Leu Glu Trp Val
        35                  40                  45

Ser Gly Ile Tyr Pro Ser Gly Arg Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140
```

-continued

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
        180                 185                 190

Ser Ser Val Val Thr Val Pro Ser Ser Leu Gly Thr Gln Thr Tyr
    195                 200                 205

Ile Cys Asn Val Asn His Lys Pro Ser Asn Thr Lys Val Asp Lys Arg
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
        260                 265                 270

Val Val Asp Val Ser His Glu Asp Pro Glu Val Lys Phe Asn Trp Tyr
    275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
        340                 345                 350

Pro Arg Glu Pro Gln Val Tyr Thr Leu Pro Pro Ser Arg Glu Glu Met
    355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln
    435                 440                 445

Lys Ser Leu Ser Leu Ser Pro Gly Lys
450                 455

<210> SEQ ID NO 10
<211> LENGTH: 214
<212> TYPE: PRT
<213> ORGANISM: Artificial Sequence
<220> FEATURE:
<223> OTHER INFORMATION: RAM01c

<400> SEQUENCE: 10

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

```
Ile Tyr Gly Thr Ser Ser Arg Ala Thr Gly Ile Pro Asp Arg Phe Ser
 50                  55                  60
Gly Ser Ala Ser Gly Thr Asp Phe Thr Leu Thr Ile Ser Arg Leu Gln
 65                  70                  75                  80
Pro Glu Asp Phe Ala Val Tyr Tyr Cys Gln Gln Tyr Gly Arg Ser Leu
                 85                  90                  95
Thr Phe Gly Gly Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
                195                 200                 205
Phe Asn Arg Gly Glu Cys
210

<210> SEQ ID NO 11
<211> LENGTH: 448
<212> TYPE: PRT
<213> ORGANISM: Artificial Sequence
<220> FEATURE:
<223> OTHER INFORMATION: RAM9hc

<400> SEQUENCE: 11

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Ile Tyr
                20                  25                  30
Ser Met Asn Trp Val Arg Gln Ala Pro Gly Lys Gly Leu Glu Trp Val
                35                  40                  45
Ser Ser Ile Gly Ser Ser Gly Gly Thr Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Gly Ser Gln Trp Leu Tyr Gly Met Asp Val Trp Gly Gln Gly Thr
                100                 105                 110
Thr Val Thr Val Ser Ser Ala Ser Thr Lys Gly Pro Ser Val Phe Pro
                115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
```

```
Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 12
<211> LENGTH: 214
<212> TYPE: PRT
<213> ORGANISM: Artificial Sequence
<220> FEATURE:
<223> OTHER INFORMATION: RAM91c

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Arg Ile Met Thr Tyr
            20                  25                  30

Leu Asn Trp Tyr Gln Gln Lys Pro Gly Lys Ala Pro Lys Leu Leu Ile
        35                  40                  45

Phe Val Ala Ser His Ser Gln Ser Gly Val Pro Ser Arg Phe Arg Gly
    50                  55                  60

Ser Gly Ser Glu Thr Asp Phe Thr Leu Thr Ile Ser Gly Leu Gln Pro
65                  70                  75                  80

Glu Asp Ser Ala Thr Tyr Tyr Cys Gln Gln Ser Phe Trp Thr Pro Leu
                85                  90                  95

Thr Phe Gly Gly Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 457
<212> TYPE: PRT
<213> ORGANISM: Artificial Sequence
<220> FEATURE:
<223> OTHER INFORMATION: RAM4hc

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Asp Trp Val Arg Gln Ala Pro Gly Lys Gly Leu Glu Trp Val
        35                  40                  45

Ser Gly Ile Val Pro Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255
```

```
Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 14
<211> LENGTH: 214
<212> TYPE: PRT
<213> ORGANISM: Artificial Sequence
<220> FEATURE:
<223> OTHER INFORMATION: RAM41c

<400> SEQUENCE: 14

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 15
<211> LENGTH: 440
<212> TYPE: PRT
<213> ORGANISM: Artificial Sequence
<220> FEATURE:
<223> OTHER INFORMATION: anti-RAM9-68-1hc

<400> SEQUENCE: 15

Gln Glu Gln Leu Lys Glu Ser Gly Gly Arg Leu Val Lys Pro Gly Gly
1               5                   10                  15

Thr Leu Thr Leu Thr Cys Lys Ala Ser Gly Met Asp Phe Asn Asn Tyr
            20                  25                  30

Tyr Tyr Met Ala Trp Val Arg Gln Ala Pro Gly Lys Gly Leu Glu Trp
            35                  40                  45

Ile Gly Tyr Ile Ser Gly Gly Ser Pro Tyr Tyr Ala Ser Trp Ala
        50                  55                  60

Lys Gly Arg Phe Thr Ile Ser Arg Thr Ser Thr Thr Val Asp Leu Lys
65              70                  75                  80

Met Thr Ser Leu Thr Thr Glu Asp Thr Ala Thr Tyr Phe Cys Gly Arg
            85                  90                  95

Tyr Thr Asp Ile Asn Asn Gly Ile Asp Leu Trp Gly Pro Gly Thr Leu
            100                 105                 110

Val Thr Val Ser Ser Gly Gln Pro Lys Ala Pro Ser Val Phe Pro Leu
            115                 120                 125

Ala Pro Cys Cys Gly Asp Thr Pro Ser Ser Thr Val Thr Leu Gly Cys
            130                 135                 140

Leu Val Lys Gly Tyr Leu Pro Glu Pro Val Thr Val Thr Trp Asn Ser
145                 150                 155                 160

Gly Thr Leu Thr Asn Gly Val Arg Thr Phe Pro Ser Val Arg Gln Ser
            165                 170                 175

Ser Gly Leu Tyr Ser Leu Ser Ser Val Val Ser Val Thr Ser Ser Ser
            180                 185                 190

Gln Pro Val Thr Cys Asn Val Ala His Pro Ala Thr Asn Thr Lys Val
            195                 200                 205

Asp Lys Thr Val Ala Pro Ser Thr Cys Ser Lys Pro Thr Cys Pro Pro
            210                 215                 220

Pro Glu Leu Leu Gly Gly Pro Ser Val Phe Ile Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Asp Asp Pro Glu Val Gln Phe Thr Trp Tyr Ile
            260                 265                 270

Asn Asn Glu Gln Val Arg Thr Ala Arg Pro Pro Leu Arg Glu Gln Gln
            275                 280                 285

Phe Asn Ser Thr Ile Arg Val Val Ser Thr Leu Pro Ile Ala His Gln
            290                 295                 300
```

Asp Trp Leu Arg Gly Lys Glu Phe Lys Cys Lys Val His Asn Lys Ala
305                 310                 315                 320

Leu Pro Ala Pro Ile Glu Lys Thr Ile Ser Lys Ala Arg Gly Gln Pro
            325                 330                 335

Leu Glu Pro Lys Val Tyr Thr Met Gly Pro Pro Arg Glu Glu Leu Ser
            340                 345                 350

Ser Arg Ser Val Ser Leu Thr Cys Met Ile Asn Gly Phe Tyr Pro Ser
            355                 360                 365

Asp Ile Ser Val Glu Trp Glu Lys Asn Gly Lys Ala Glu Asp Asn Tyr
    370                 375                 380

Lys Thr Thr Pro Ala Val Leu Asp Ser Asp Gly Ser Tyr Phe Leu Tyr
385                 390                 395                 400

Ser Lys Leu Ser Val Pro Thr Ser Glu Trp Gln Arg Gly Asp Val Phe
                405                 410                 415

Thr Cys Ser Val Met His Glu Ala Leu His Asn His Tyr Thr Gln Lys
                420                 425                 430

Ser Ile Ser Arg Ser Pro Gly Lys
            435                 440

<210> SEQ ID NO 16
<211> LENGTH: 215
<212> TYPE: PRT
<213> ORGANISM: Artificial Sequence
<220> FEATURE:
<223> OTHER INFORMATION: anti-RAM9-68-11c

<400> SEQUENCE: 16

Asp Ile Val Met Thr Gln Thr Pro Ser Ser Val Ser Glu Pro Val Gly
1               5                   10                  15

Gly Thr Val Thr Ile Asn Cys Gln Ala Ser Glu Asn Ile Tyr Ser Asn
            20                  25                  30

Leu Ala Trp Tyr Gln Gln Lys Pro Gly Gln Pro Pro Lys Leu Leu Ile
        35                  40                  45

Tyr Leu Ala Ser Ser Leu Thr Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Ile Tyr Tyr Cys Gln Asn Asn Tyr Gly Asp Val Arg
                85                  90                  95

Tyr Gly Arg Asn Ala Phe Gly Gly Gly Thr Glu Val Val Val Lys Gly
            100                 105                 110

Asp Pro Val Ala Pro Thr Val Leu Ile Phe Pro Pro Ala Ala Asp Gln
        115                 120                 125

Val Ala Thr Gly Thr Val Thr Ile Val Cys Val Ala Asn Lys Tyr Phe
    130                 135                 140

Pro Asp Val Thr Val Thr Trp Glu Val Asp Gly Thr Thr Gln Thr Thr
145                 150                 155                 160

Gly Ile Glu Asn Ser Lys Thr Pro Gln Asn Ser Ala Asp Cys Thr Tyr
                165                 170                 175

Asn Leu Ser Ser Thr Leu Thr Leu Thr Ser Thr Gln Tyr Asn Ser His
            180                 185                 190

Lys Glu Tyr Thr Cys Lys Val Thr Gln Gly Thr Thr Ser Val Val Gln
        195                 200                 205

Ser Phe Asn Arg Gly Asp Cys
    210                 215

<210> SEQ ID NO 17
<211> LENGTH: 442
<212> TYPE: PRT
<213> ORGANISM: Artificial Sequence
<220> FEATURE:
<223> OTHER INFORMATION: anti-RAM9-54-5hc

<400> SEQUENCE: 17

```
Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Gly Tyr
            20                  25                  30

Asp Met Cys Trp Val Arg Gln Ala Pro Gly Lys Gly Leu Glu Trp Ile
        35                  40                  45

Ala Cys Ile Tyr Asp Gly Asp Val Arg Thr Tyr Tyr Ala Ser Trp Ala
    50                  55                  60

Lys Gly Arg Phe Thr Ile Ser Arg Thr Ser Thr Thr Met Thr Leu
65                  70                  75                  80

Gln Met Thr Gly Leu Thr Ala Ala Asp Thr Ala Thr Tyr Leu Cys Ala
            85                  90                  95

Arg Gly Ala Ser Gly Tyr Leu Ser Ala Leu Tyr Leu Trp Gly Pro Gly
        100                 105                 110

Thr Leu Val Thr Val Ser Ser Gly Gln Pro Lys Ala Pro Ser Val Phe
    115                 120                 125

Pro Leu Ala Pro Cys Cys Gly Asp Thr Pro Ser Ser Thr Val Thr Leu
130                 135                 140

Gly Cys Leu Val Lys Gly Tyr Leu Pro Glu Pro Val Thr Val Thr Trp
145                 150                 155                 160

Asn Ser Gly Thr Leu Thr Asn Gly Val Arg Thr Phe Pro Ser Val Arg
            165                 170                 175

Gln Ser Ser Gly Leu Tyr Ser Leu Ser Ser Val Val Ser Val Thr Ser
        180                 185                 190

Ser Ser Gln Pro Val Thr Cys Asn Val Ala His Pro Ala Thr Asn Thr
    195                 200                 205

Lys Val Asp Lys Thr Val Ala Pro Ser Thr Cys Ser Lys Pro Thr Cys
210                 215                 220

Pro Pro Pro Glu Leu Leu Gly Gly Pro Ser Val Phe Ile Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser Gln Asp Pro Glu Val Gln Phe Thr Trp
        260                 265                 270

Tyr Ile Asn Asn Glu Gln Val Arg Thr Ala Arg Pro Pro Leu Arg Glu
    275                 280                 285

Gln Gln Phe Asn Ser Thr Ile Arg Val Val Ser Thr Leu Pro Ile Ala
290                 295                 300

His Gln Asp Trp Leu Arg Gly Lys Glu Phe Lys Cys Lys Val His Asn
305                 310                 315                 320

Lys Ala Leu Pro Ala Pro Ile Glu Lys Thr Ile Ser Lys Ala Arg Gly
            325                 330                 335

Gln Pro Leu Glu Pro Lys Val Tyr Thr Met Gly Pro Pro Arg Glu Glu
        340                 345                 350

Leu Ser Ser Arg Ser Val Ser Leu Thr Cys Met Ile Asn Gly Phe Tyr
    355                 360                 365
```

```
Pro Ser Asp Ile Ser Val Glu Trp Glu Lys Asn Gly Lys Ala Glu Asp
    370             375             380
Asn Tyr Lys Thr Thr Pro Ala Val Leu Asp Ser Asp Gly Ser Tyr Phe
385             390             395             400
Leu Tyr Ser Lys Leu Ser Val Pro Thr Ser Glu Trp Gln Arg Gly Asp
            405             410             415
Val Phe Thr Cys Ser Val Met His Glu Ala Leu His Asn His Tyr Thr
                420             425             430
Gln Lys Ser Ile Ser Arg Ser Pro Gly Lys
            435             440

<210> SEQ ID NO 18
<211> LENGTH: 212
<212> TYPE: PRT
<213> ORGANISM: Artificial Sequence
<220> FEATURE:
<223> OTHER INFORMATION: anti-RAM9-54-51c

<400> SEQUENCE: 18

Asp Val Val Met Thr Gln Thr Pro Ala Ser Val Ser Glu Pro Val Gly
1               5                   10                  15
Gly Thr Val Thr Ile Lys Cys Gln Ala Ser Phe Thr Ile Thr Ser Asn
            20                  25                  30
Leu Ala Trp Tyr Gln Gln Lys Pro Gly Gln Pro Pro Lys Leu Leu Ile
        35                  40                  45
Tyr Gly Ala Ser Asn Leu Ala Ser Gly Val Ser Ser Arg Phe Arg Gly
    50                  55                  60
Ser Gly Phe Gly Thr Glu Phe Thr Leu Thr Ile Ser Asp Leu Glu Cys
65                  70                  75                  80
Ala Asp Ala Ala Thr Tyr Tyr Cys Gln Cys Ala Ala Val Leu Ser Ser
                85                  90                  95
Trp Thr Phe Gly Gly Gly Thr Glu Val Val Lys Gly Asp Pro Val
            100             105             110
Ala Pro Thr Val Leu Ile Phe Pro Pro Ala Ala Asp Gln Val Ala Thr
        115                 120                 125
Gly Thr Val Thr Ile Val Cys Val Ala Asn Lys Tyr Phe Pro Asp Val
    130                 135                 140
Thr Val Thr Trp Glu Val Asp Gly Thr Thr Gln Thr Thr Gly Ile Glu
145                 150                 155                 160
Asn Ser Lys Thr Pro Gln Asn Ser Ala Asp Cys Thr Tyr Asn Leu Ser
                165                 170                 175
Ser Thr Leu Thr Leu Thr Ser Thr Gln Tyr Asn Ser His Lys Glu Tyr
            180                 185                 190
Thr Cys Lys Val Thr Gln Gly Thr Thr Ser Val Val Gln Ser Phe Asn
        195                 200                 205
Arg Gly Asp Cys
    210
```